(12) United States Patent
Huang

(10) Patent No.: US 7,673,525 B2
(45) Date of Patent: Mar. 9, 2010

(54) SENSOR SYSTEM FOR PIPE AND FLOW CONDITION MONITORING OF A PIPELINE CONFIGURED FOR FLOWING HYDROCARBON MIXTURES

(75) Inventor: Songming Huang, Hardwick (GB)

(73) Assignee: Schlumberger Technology Corporation, Cambridge, MA (US)

( * ) Notice: Subject to any disclaimer, the term of this patent is extended or adjusted under 35 U.S.C. 154(b) by 365 days.

(21) Appl. No.: 11/621,167

(22) Filed: Jan. 9, 2007

(65) Prior Publication Data

US 2008/0163700 A1    Jul. 10, 2008

(51) Int. Cl.
*G01F 1/66* (2006.01)
*G01F 1/68* (2006.01)

(52) U.S. Cl. .................................................. 73/861.25
(58) Field of Classification Search ........................ None
See application file for complete search history.

(56) References Cited

U.S. PATENT DOCUMENTS

| | | | |
|---|---|---|---|
| 3,913,378 | A | 10/1975 | Hausler |
| 4,718,774 | A | 1/1988 | Slough |
| 4,770,184 | A | 9/1988 | Greene, Jr. et al. |
| 4,787,252 | A * | 11/1988 | Jacobson et al. ........ 73/861.28 |
| 5,092,176 | A | 3/1992 | Buttram et al. |
| 5,327,893 | A | 7/1994 | Savic |
| 6,470,749 | B1 | 10/2002 | Han et al. |
| 6,513,385 | B1 | 2/2003 | Han et al. |
| 6,575,043 | B1 | 6/2003 | Huang et al. |
| 6,758,100 | B2 | 7/2004 | Huang |
| 6,886,406 | B1 | 5/2005 | Couet et al. |
| 7,430,903 | B2 | 10/2008 | Ramos |
| 2003/0010125 | A1 | 1/2003 | Han et al. |
| 2005/0011278 | A1 * | 1/2005 | Brown et al. ............ 73/861.18 |
| 2006/0214098 | A1 | 9/2006 | Ramos |
| 2007/0006656 | A1 * | 1/2007 | Batzinger et al. ............ 73/606 |
| 2008/0163692 | A1 | 7/2008 | Huang |

FOREIGN PATENT DOCUMENTS

FR        2266869 A1    10/1975

(Continued)

OTHER PUBLICATIONS

Andersen et al Ultrasonic instrumentation for on-line monitoring of solid deposition in pipes SPE Production Operations Symposium, Oklahoma City, Mar. 9-11, 1997, SPE 37437.

(Continued)

*Primary Examiner*—Hezron Williams
*Assistant Examiner*—Rose M Miller
(74) *Attorney, Agent, or Firm*—James McAleenan; Helene Raybaud; Jody Lynn DeStefanis

(57) ABSTRACT

Embodiments of the present invention provide systems and methods for reliable and accurate flow assurance and pipeline monitoring. More specifically but not by way of limitation, systems and methods of the present invention provide for using Doppler profiles through a pipeline section to monitor and/or measure depositing on and corrosion of a pipeline configured for flowing one or more hydrocarbons. In other embodiments of the present invention, thermal probe sensors may be used to monitor the depositing on and corrosion of the section of the pipeline. And in still further embodiments, combinations of Doppler sensors, thermal sensors and/or acoustic impedance sensors are provided with outputs from one or more of the sensors used to control one or more of the sensors or to provide for determination of flow assurance or pipeline monitoring.

28 Claims, 12 Drawing Sheets

FOREIGN PATENT DOCUMENTS

| | | | |
|---|---|---|---|
| GB | 2 343 249 B | 1/2001 |
| GB | 2 363 455 B | 10/2002 |
| GB | 2 369 680 B | 4/2004 |
| JP | 6191509 A | 5/1986 |
| WO | 9936919 A1 | 8/1999 |
| WO | 01/31328 A1 | 5/2001 |
| WO | 2005/088262 A2 | 9/2005 |

OTHER PUBLICATIONS

Coulson et al. Heat transfer Chemical Engineering, Pergamon Press, Oxford, vol. 1, $3^{rd}$ edition, 1977, pp. 188-191.

Dukler et al A model for gas-liquid slug flow in horizontal and near horizontal tubes Industrial and Engineering Chemistry Fundamentals, vol. 14, No. 4, 1975, pp. 337-347.

Gunarathne et al Novel techniques for monitoring and enhancing dissolution of mineral deposits in petroleum pipelines Offshore Europe Conference, Aberdeen, Sep. 5-8, 1995, SPE 30418.

Hayman et al High-resolution cementation and corrosion imaging by ultrasound SPWLA $32^{nd}$ Annual Logging Symposium, Jun. 16-19, 1991, pp. 1-25.

Nicholson et al Intermittent two phase flow in horizontal pipes: predictive models Can. J. Chem. Eng., vol. 56, 1978, pp. 653-663.

Perry Introduction Hot-wire anemometry, Oxford University Press, New York 1982, pp. 1-6.

\* cited by examiner

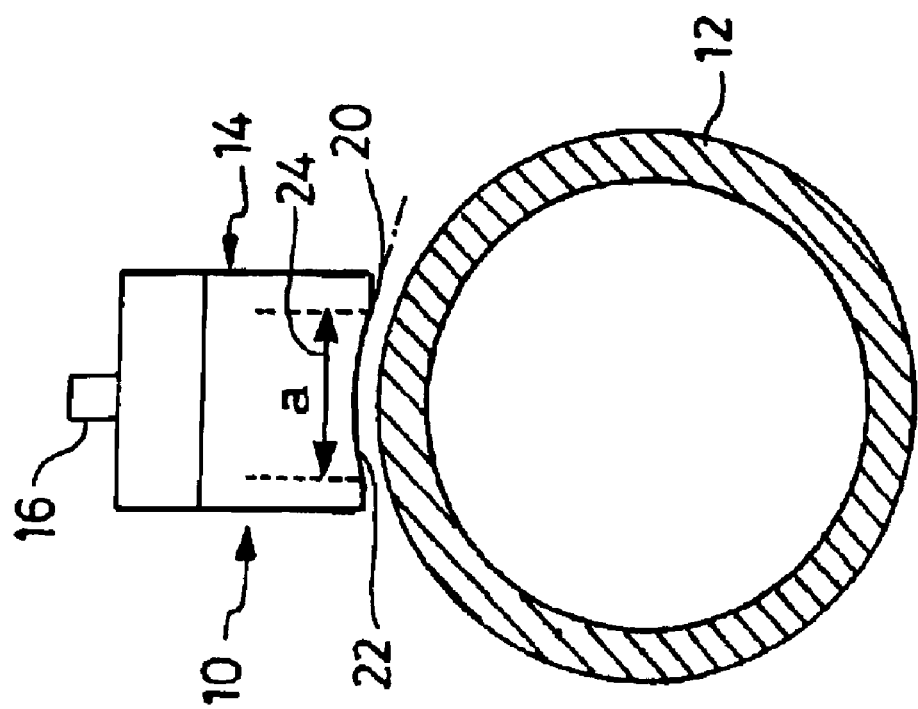

SENSOR SYSTEM FOR PIPE AND FLOW CONDITION MONITORING OF A PIPELINE CONFIGURED FOR FLOWING HYDROCARBON MIXTURES

This application is related to U.S. application Ser. No. 11/621,154, filed on a date even herewith by Songming Huang and entitled "System and Method for Using Thermal Sensor Probes for Flow Analysis, Flow Assurance and Pipe Condition Monitoring of a Pipeline for Flowing Hydrocarbons", the entire disclosure of which is incorporated herein by reference for all purposes.

BACKGROUND

An embodiment of the invention provides for Doppler sensor monitoring of pipe and flow conditions of a pipeline for flowing hydrocarbon mixtures. More specifically, but not by way of limitation, in an embodiment of the present invention, one or more Doppler sensors may be configured to sense a profile through a section of the pipeline that may be provided to a processor that may compare the profile with previous profiles through the section of pipeline to determine depositing on and/or corrosion to the section of pipeline. Doppler output from the sensor regarding the flow of the hydrocarbon mixture may be combined with the profile for analysis of deposits and/or corrosion and/or to provide for the management of the sensing of the section of the pipeline by the Doppler sensor. In some embodiments, a network of Doppler sensors may be configured to provide for flow assurance and/or monitoring of pipe condition in a pipeline transporting hydrocarbons, and in particular, but not by way of limitation, a network of noninvasive sensors whose output is data-fused to determine properties of the pipeline and flow through the pipeline. In certain aspects the network of Doppler sensors may further comprise acoustic impedance sensors and/or thermal probe sensors.

Pipe condition monitoring, flow condition monitoring and flow assurance are important in oilfield production systems, particularly subsea systems with long tiebacks, and hydrocarbon transportation pipelines. In such production systems and pipelines, various scale depositions may occur in part or all of the pipeline, production conduits or the like during the life of a production well or a transportation pipeline. These scale deposits may be the principle causes of flow assurance problems.

The term scale may be used to describe various organic and mineral deposits on the pipe wall, such as asphaltenes, waxes, hydrates or the like. Wax and asphaltene depositions, due to the cooling effect of seawater, may be a main concern for sub-sea tieback systems. Mineral scales may be associated with production pipelines and the like being caused by water breakthrough during production. Currently scale inhibition and/or remediation strategies may only be based on laboratory analysis of fluids retrieved from the production systems and transportation pipelines. The information from such analysis may be of limited value because it is not conducive to real-time understanding and management. Furthermore, In the case of remediation management, the current flow and pipeline analysis systems provide no feedback information on the effect of the remediation treatment. This may lead to productivity decrease due to under-treatment or undue treatment cost due to over treatment.

Pipeline corrosion is an important issue for production and transportation systems. For example, if sand erosion or the like occurs during oil production, then there is a significant possibility of sand damage to any anti-corrosion coatings that may have been applied inside the pipes, conduits and/or the like of the oil production or oil transportation systems. As such, this sand damage to the oil production or oil transportation systems may lead to corrosion of the pipes and/or conduits of the oil production or oil transportation systems. Moreover, serious corrosion should be detected and repaired in time to prevent accidental occurrences, such as hydrocarbon spills or the like, which may be extremely significant in subsea or remote locations. Other applications of flow assurance and pipeline monitoring include the detection of abnormal conditions in the production or transportation of hydrocarbons. For example, in a subsea gas production system, liquid may accumulate and produce slug flow conditions that may overload a surface handling system. An early warning system as to the arrival time of such slugs may allow timely control measures to be taken to prevent system overloading. A real time monitoring system on the seabed pipeline may also detect events such as water breakthrough long before it reaches the surface facility.

U.S. Pat. No. 6,758,100 ("the '100 patent") describes a clamp-on ultrasonic multiphase flow meter based on range-gated (pulsed) Doppler measurements. In the '100 patent, Doppler data is used to derive flow velocities and phase fractions. The entire disclosure of the '100 patent is hereby incorporated by reference for all purposes.

U.S. Pat. No. 6,575,043 ("the '043 patent") describes a non-invasive clamp-on multi-phase flow meter based on an acoustic impedance measurement principle. Identification of liquid and gas phases inside the pipe in the '043 patent is achieved by measuring the acoustic impedance of the material in contact with the pipe wall, and a velocity measurement is performed by cross-correlating impedance signals from two measurements separated by a known distance along the axial direction of the pipe. The entire disclosure of the '043 patent is hereby incorporated by reference for all purposes.

SUMMARY

Embodiments of the present invention provide systems and methods for reliable and accurate flow assurance and pipeline monitoring. More specifically but not by way of limitation, systems and methods of the present invention provide for using Doppler profiles through a pipeline section to monitor and/or measure depositing on and corrosion of a pipeline configured for flowing one or more hydrocarbons. In other embodiments of the present invention, thermal probe sensors may be used to monitor the depositing on and corrosion of the section of the pipeline.

In certain embodiments of the present invention, methods and systems are described that use multiple diverse-modality sensors with a data fusion processor to provide for flow assurance and pipeline monitoring. Such embodiments may provide flow assurance and pipe monitoring systems that are reliable in detecting abnormal conditions and provide for flow assurance and pipeline monitoring for a much wider range of flow regimes. In certain aspects, the multiple diverse-modality sensors may comprise Doppler sensors, thermal probe sensors and/or acoustic impedance sensors.

In an embodiment of the present invention, multiple diverse-modality sensors may be configured with a data fusion processor. The measurements performed by such an embodiment may be distributed in space and time and may be diverse in modality. The measurements from the multiple diverse-modality sensors, which may be independent or inter-correlated with each other, may be combined in a data fusion unit, where the required output parameters, such as the flow rates, phase fractions, flow regime, slug parameters, water content, thickness and type of scale deposit, corrosion status and/or the like may be derived. In certain aspects, real-time updating of the measurements and/or analysis may provide a trend-tracking tool, which may provide for processing of dynamic information, such as scale build up rate, water content increase rate, and/or the like. Embodiments of the present invention may provide for multi-sensor data fusion and result in a more reliable monitoring system that may reduce the chances of both false-alarm and missed-detection.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings.

BRIEF DESCRIPTION OF THE DRAWINGS

In the figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

The invention will now be described, by way of example, and with reference to the accompanying drawings, in which:

FIG. 1A illustrates a partial sectional view across a pipe non-invasively coupled with a Doppler sensor, in accordance with an embodiment of the present invention;

DETAILED DESCRIPTION

Figure 1B:
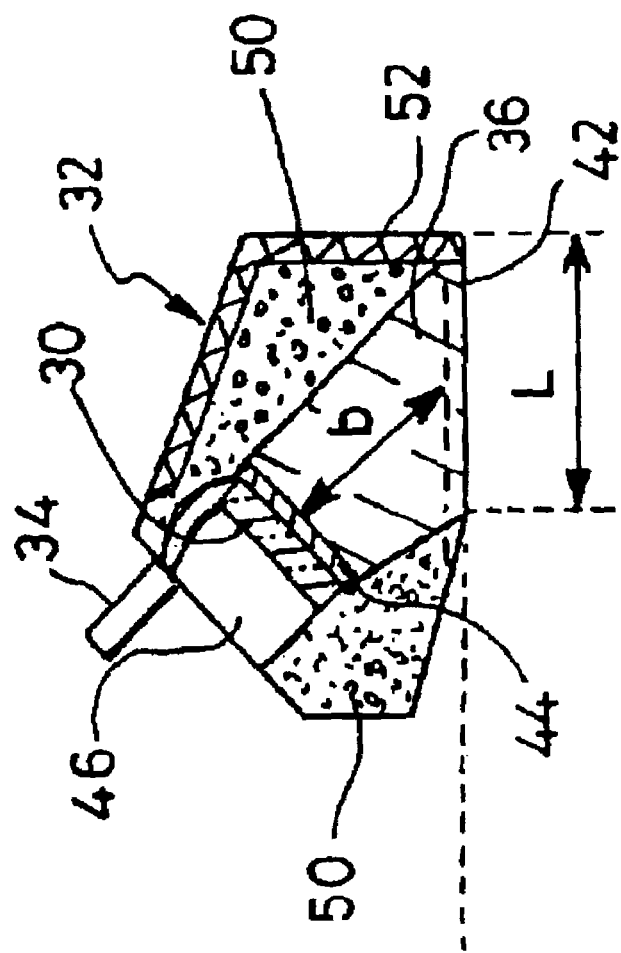
FIG. 1B shows a schematic-type illustration of vertical section through a Doppler sensor, in accordance with an embodiment of the present invention.

Embodiments of the present invention provide systems and methods for reliable and accurate flow assurance and pipeline monitoring. More specifically but not by way of limitation, systems and methods of the present invention provide for using Doppler profiles through a pipeline section to monitor and/or measure depositing on and corrosion of a pipeline configured for flowing one or more hydrocarbons. In other embodiments of the present invention, thermal probe sensors may be used to monitor the depositing on and corrosion of the section of the pipeline. And in still further embodiments, combinations of Doppler sensors, thermal sensors and/or acoustic impedance sensors are provided with outputs from one or more of the sensors used to control one or more of the sensors or to provide for determination of flow assurance or pipeline monitoring.

FIG. 1A illustrates a partial sectional view across a pipe non-invasively coupled with a Doppler sensor, in accordance with an embodiment of the present invention. In an embodiment of the present invention, a Doppler sensor 10 may be clamped to a pipe 12 (shown in vertical section), where the pipe 12 may comprise a section of a pipeline for flowing hydrocarbon mixtures. The Doppler sensor 10 may comprise a probe 14, which may surround a transceiver (not shown), and a connector 16—that in use may be connected to signal processing equipment. In certain aspects, a lower face 20 of the probe 14 may have a groove 22 machined across a central portion 24. Curvature of the groove 22 may be selected to be complimentary to that of an outer surface of the pipe 12. As such, the central portion 24 may engage with the pipe when the Doppler sensor 10 is clamped onto the pipe 12. This configuration may ensure that sufficient energy is transmitted from the probe 14 into a wall of the pipe 12.

This Doppler sensor 10 may be applicable to horizontal pipes carrying multi-phase fluid flow and in certain circumstances to vertical pipes with multi-phase flow. The Doppler sensor 10 may consist of at least one narrow band ultrasonic transducer probe, which may be mounted on the external surface of a flow conveying pipe, and may include a sound absorbing block which may be mounted to the front of the probe to attenuate unwanted energy reflections in the pipe wall. Merely by way of example, the transducer probe may emit signal pulses in a frequency range of 100 KHz to 10 MHz. As such, short bursts of a narrow-band energy may be emitted into the flow and echoes may be received that are frequency shifted by moving reflectors, such as phase boundaries in the multiphase mixture following in the pipe 12, according to the Doppler effect. The frequency shift observed for the reflected signed may provides a measure of average velocity, and the energy associated with the Doppler signal may also be calculated to assist with discriminating between different phases in the flow.

Doppler frequency shift and energy signals from different viewing angles around the circumference of the pipe 12 may be obtained by moving the Doppler sensor 10 sequentially to different angular positions, or by mounting multiple Doppler sensors 10 at these positions and acquiring data through a multiplexer. Doppler energy and frequency shift information generated at all such positions may be combined, through appropriate signal processing, to produce the liquid holdup and liquid flow rate. Gas velocity may derived from a traveling velocity of liquid slugs, which are areas where the entire cross-section of the pipe is filled with liquid, and the velocity of the liquid slugs in turn is obtained from cross-correlation of Doppler energy signals from at least two probes having a known separation along the flow direction.

The Doppler sensor 10 may be used for monitoring of two-phase flows, surface monitoring of liquid production from gas wells, and liquid and gas flow metering for oil wells. For three-component producing wells where water forms a stratified layer towards the bottom of a pipe, water holdup may be measured by combining range-gated Doppler profiles from different viewing angles, using a tomography approach. Thus a three-phase flowmeter may be formed from the Doppler sensor 10.

A clamp-on non-invasive flowmeter for use on industrial pipelines has many advantages in that it is applicable to either periodic testing or permanent installation since there is no disruption to the industrial/production process during monitoring of the flow, and no production down-time for maintenance even when the meter is permanently installed. The flowmeter is also compact and light as no fluid conduit is used as part of the meter.

FIG. 1B shows a schematic-type illustration of vertical section through a Doppler sensor, in accordance with an embodiment of the present invention. As illustrated in FIG. 1B, the Doppler sensor 10 may comprise a transceiver 30, a housing 32 and a connector 34. The transducer crystal 30 may be mounted on an angled probe wedge 36 which may be made from a hard material, e.g. black Perspex or the like, that may provide an ultrasound transmission path from the crystal 30 to a contact face 42 that may be disposed to contact a pipe surface when the Doppler sensor 10 is in use. An impedance matching layer 44 may be used between the crystal 30 and the transmission path rod 36 to improve energy coupling. The diameter of the transmission path rod 36 may be slightly larger than that of the crystal disc 30. Merely by way of example, ranges between 10 to 25 mm may be used depending upon the frequency at which the disc 30 is designed to operate, with the length of the transmission path inside the probe, b, for such ranges being of the order of 10s of millimeters.

The gap between the transmission path rod 36 and the housing 32 may be filled with a sound absorbing material 50—such as epoxy, rubber loaded with solids, such as metal particles, and/or the like. An inner surface 52 at the front part of the probe housing 32 may be configured to be highly scattering and may provide for minimization of specular reflections. Merely by way of example, the front part of the probe housing 32 may be configured as a saw tooth shape. In certain aspects, to narrow the bandwidth of the signal transmitted from the transceiver 30 and increase the sensitivity of the transceiver when receiving reflected signals and/or the like, no damping material may be applied to the region 46 behind the crystal 30.

The sound absorbing material 50 used in certain embodiments of the present invention may be used because in metal pipes there is a large mismatch between the acoustic impedance of the pipe wall material and that of the liquid in the pipe. In such cases, only a small fraction of energy is transmitted into the liquid each time the ultrasound signal strikes at the pipe-wall/liquid interface. A much larger portion of the energy is reflected by the two sides of the wall, forming a zigzag traveling path along the axial direction, and meanwhile this in-wall energy will also spread circumferentially as it travels forward. The multiple reflections described above results in multiple point and multiple delayed energy entry into the liquid, with delay step determined by the wave traveling time between two successive entry points. This wave propagation pattern in the pipe wall complicates the interpretation of the Doppler measurements from the Doppler sensor 10. For instance, an echo received in a late range gate channel may be caused by a reflector at a greater depth, or by one at a much shallower depth but further away along the axial direction; there is no way to tell. It is therefore not possible, in such a case, to obtain a true Doppler profile measurement across the flow.

The use, in an embodiment of the present invention, of a sound absorbing block coupled to the transducer 30 may overcome this problem. The block may be made by molding a mixture of epoxy and tungsten powder and configuring a contact face fit for the Doppler sensor 10 to the curvature of the pipe. At least a 50:50 volume mixing ratio may be used to achieve a high acoustic impedance of around 20 Mrayls, which is much better matched to the impedance of the wall material of the pipe (45 Mrayls for steel) than that of liquid (1.5 Mrayls for water). With such an impedance match, at least 70% of the energy from the Doppler sensor 10 may be absorbed each time when a wave from the Doppler sensor 10 encounters the block/pipe interface. In certain aspects, a mixture of epoxy and tungsten powder may also provide for attenuation of ultrasound signals.

The dimension of the block in an axial direction, x, (not shown) may at least cover one beam width in the pipe wall, (which is related to the axial contact length, L, of the probe and the beam diverging angle in the pipe). In certain aspects a configuration with x>3L may be used. In certain aspects, the circumferential contact length of the block with the pipe, w, may be at least twice that of the transducer probe. In aspects of the present invention, the height of the block may be of the order of at least 10s of millimeters and may provide for attenuation of the energy trapped inside. Ultrasonic coupling gel, such as shear wave coupling gel or the like, may be applied between the contact face of the block and the pipe, and the block and, in some aspects the block may be pressed against the pipe wall by pressing means, such as mechanical clamps or the like, to ensure good energy coupling.

Figure 2A:
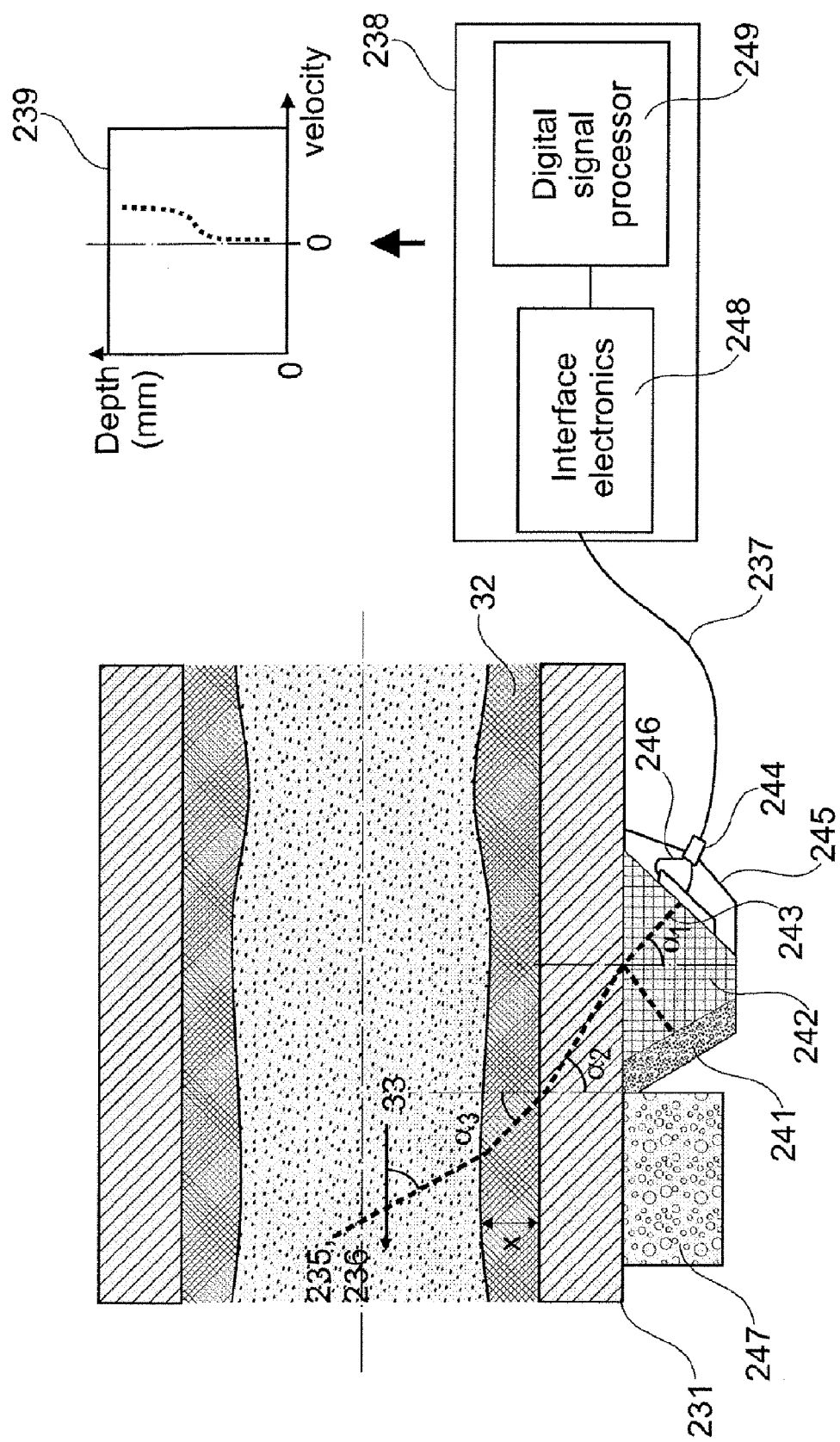
FIG. 2A provides a schematic-type illustration of scale thickness sensor comprising a range-gated ultrasonic Doppler measurement and processing configuration coupled with a pipeline, in accordance with an embodiment of the present invention.

FIG. 2A provides a schematic-type illustration of scale thickness sensor comprising range-gated ultrasonic Doppler measurement and processing configuration coupled with a pipeline, in accordance with an embodiment of the present invention. In the embodiment depicted in n FIG. 2A, an ultrasonic sensor probe may be clamped onto the metal pipe carrying a fluid with its sensing face pressed firmly against a pipe wall 231. For a horizontal pipe, more than one probe may be mounted at different circumferential positions around the pipe in case the scale deposits are different at these locations.

In certain aspects, at least one probe may be mounted as close as possible to the bottom of the pipe, where, when a multi-phase mixture is flowing through the pipe, the liquid phase of the mixture may always be in contact with the pipe wall 231. The sensor probe may be an ultrasonic Doppler probe comprising a piezoelectric ceramic crystal 243, a pipe interface block 242, a sound absorbing/scattering material 241, a plurality of connecting wires 246, a probe housing 245 and a feed-through electrical connector 244. For subsea deep sea applications and/or the like, the probe housing 245 may be configured to be pressure-resistant.

In certain aspects, in order to minimize the effect of multiple reflections inside the pipe wall 231, an optional sound absorbing block 247 that may be impedance matched to the material forming the pipe wall 231 may be used. The probe may be an angled one, in which the incident angle ($\alpha_1$) of an ultrasonic beam to the pipe wall 231 may be set to such a value that only a shear wave is generated in the pipe wall 231, in accordance with the refraction law:

$$\frac{\sin\alpha_1}{c_1} = \frac{\sin\alpha_2}{c_2} \qquad (1)$$

where $c_1$, $\alpha_1$ are respectively the wave velocity and incident angle in the interface block 242, which may in certain aspects comprise a plastic material, and $c_2$, $\alpha_2$ are respectively the velocity and angle of the refracted wave in the pipe wall 231. In certain aspects of the present invention, the angle $\alpha_2$ may range between 38~70 degrees. In such aspects, the refracted wave in the pipe wall 231, where the pipe wall 231 comprises steel, may be a shear wave with a value of $c_2$=3230 m/s.

In certain aspects, to achieve a narrow frequency band, only air/gas may be disposed around the backside of the piezoelectric element, with no damping material. The size of the piezoelectric element may be selected according to the interrogating frequency required. In one embodiment of the present invention, a frequency ranges from 0.5 to 20 MHz may be used. Higher frequencies may result in higher thickness measurement resolutions. In certain aspects, frequency ranges from 2 MHz to 10 MHz may be used depending on the requirements of a specific application. An electrical cable 237 may be used to connect the ultrasonic sensor probe to an electronics unit 238. The electronics unit 238 may be used to operate the ultrasonic probe in a pulse-echo mode.

In one embodiment of the present invention one or more Doppler sensors/probes may be positioned around/along a section of a pipeline and the outputs from the one or more Doppler sensors/probes may be processed to provide for detection of scale on the wall of the section of the pipeline. From this scale detection, flow assurance and/or pipe maintenance may be assessed. The processor may display the output of scale detection, put the output in a memory, manage a scale control system, output the processed scale data to another processor and/or the like.

In an embodiment of the present invention, in an operating cycle, the electronics unit 238 may apply a narrow band electrical pulse, which may consists of several cycles of a sinusoidal wave and in certain aspects may be of the order of 2 to 8 cycles, to the piezoelectric element that, in turn, may generate a narrow band ultrasonic pulse. A narrow frequency band of the emitted energy may, in certain aspects, make detection of frequency shift due to Doppler effect easier. In the described embodiment, ultrasonic energy 235 is transmitted through the pipe interface block 242, the pipe wall 231, a scale deposit layer 232 and into a fluid 233.

An echo 236 of the ultrasonic energy 235 may be generated wherever the ultrasonic energy 235 meets interfaces between different acoustic impedances. Some of these interfaces may be static, such as that between the pipe wall 231 and the scale layer 232 and that between the scale layer 232 and the fluid 233. Other interfaces may be dynamic, such as solid particles, liquid droplets, gas bubbles or the like traveling with the fluid 233 and through the zone being analyzed by the Doppler sensors/probes. Only moving reflectors, such as those entrained in fluid 233, will produce a Doppler frequency shift to the corresponding echoes. Echoes from static interfaces will contain only energy at the original emission frequency, $f_e$, because of the lack of Doppler frequency shifting form such static interfaces.

After emitting the pulse of the ultrasonic energy 235, the interface electronics 248 may switch into an echo-recording mode. In other embodiments, separate echo-recording devices may be used and may be positioned at different locations and/or orientations to the interface electronics 248 producing the pulse. Ultrasonic echoes during a selected time interval, which corresponds to the round-trip traveling time of the pulse-echo within a selected depth range, may be recorded by the interface electronics 248. In certain embodiments, a depth range may be selected so that it covers not only the maximum thickness of the scale layer desired to be measured, but also some distance into the flowing fluid. This may provide that a contrast between the static deposit and moving fluid may be obtained and processed. However, in certain aspects, the range may be selected so that it is not much greater than needed for the purpose of scale detection, in order to avoid unnecessary data-handling burden to the signal processing system.

In some embodiments, using pipe dimensions, prior scale depth readings and/or the like, the Doppler sensors/probes may be configured to provide for a depth range that covers the inner pipe wall, the thickness of the scale plus at least a range of the order of millimeters to 10s of millimeters into the flowing fluid. The interface electronics 248 may repeat pulse-echo cycle at a selected pulse repetition frequency, $f_{prf}$, to provide for periodic, continuous or the like analysis of the scale. In some embodiments of the present invention, a certain number of pulse-echo cycles may be carried out after a predetermined period of time. In other embodiments, a processor, which may be located at the surface, a control location, subsea and/or the like may manage the pulse-echo cycling to manage the scale detection process. In certain aspects, the management of the scale detection may be combined with a scale removal/inhibition treatment of the pipeline, section of pipeline and/or the like.

Figure 2B:
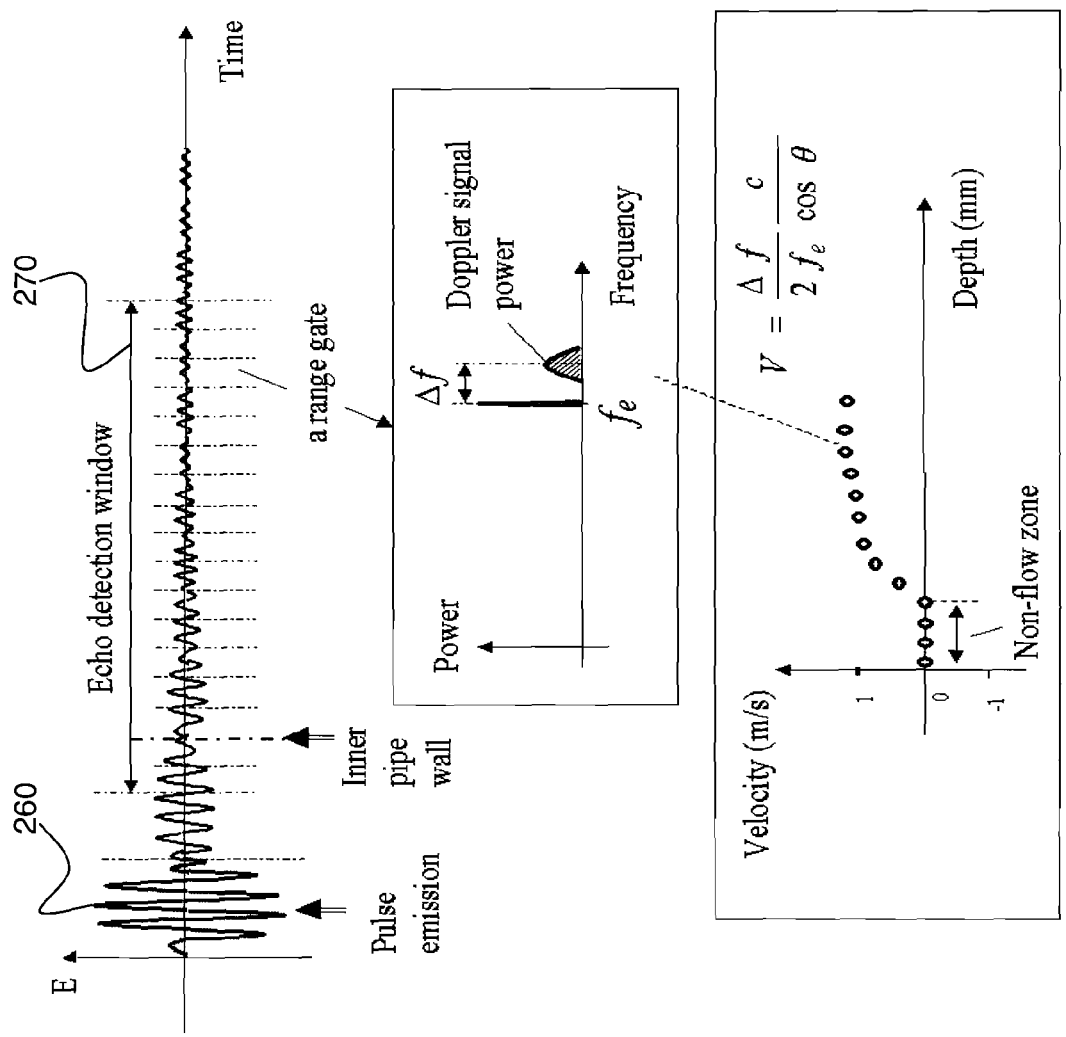
FIG. 2B illustrates Doppler profile generation and analysis, in accordance with an embodiment of the present invention.

FIG. 2B illustrates Doppler profile generation and analysis, in accordance with an embodiment of the present invention. A time domain waveform illustrates a voltage 260 that may be applied across the piezoelectric element during entire pulse-echo cycle. For the purpose of scale detection, one can select an interrogation or detection window 270 from a location inside the pipe wall to a few centimeters into the pipe bore. In an embodiment for monitor corrosion as well as scale build up, the window 270 should start from a position inside the pipe wall.

The time-domain signal in the detection window is divided into a number of fine time intervals, known as range gates. The echo signal inside each gate may be analyzed separately. In an embodiment of the present invention, a spectral analysis may be performed and appropriate filtering may be applied to separate the energy that has been frequency shifted due to the Doppler effect from that at the original emission frequency. Combining the results of the processing from all the range gates may produce one of the following profiles.

Flow velocity profile—in this the velocity at the ith range gate is produced from:

$$V_i = \frac{c}{2\cos\theta} \frac{\Delta f}{f_e} \qquad (2)$$

where c is the sound velocity, $\theta$ is the angle sustained between the ultrasonic beam and the flow direction, $f_e$ is the emission frequency and $\Delta f$ is the average Doppler frequency shift.

Doppler energy profile—in this the area under the frequency shifted spectrum is obtained by integration, and the result is the Doppler energy for the given range gate.

Such Doppler profiles may provide information on the flow region and static deposit region in the pipe. For instance, the region with scale deposition is shown by the section of points with zero velocity. Similarly on a Doppler energy profile, the scaled region is represented by points with zero Doppler energy. In an embodiment of the present invention, a reference profile obtained when the detection device was first installed or a profile from a point in time when other scale analysis techniques had been performed, when the pipe section was new and/or the like may be compared with the present profile to process the scale build up, thickness and/or the like. In some embodiments of the present invention, to reduce noise effects, increase accuracy or the like, Doppler profiles produced from a number of consecutive pulse-echo cycles may be averaged to produce a profile. In an embodiment of the present invention for monitoring the growth of the scale layer in real-time, profiles may be processed frequently, periodically, continuously or the like and compared with a reference profile, a previous profile and/or the like. In certain aspects, the range gated Doppler sensors/probes may achieve update rates of greater than 1 Hz.

Figure 3A:
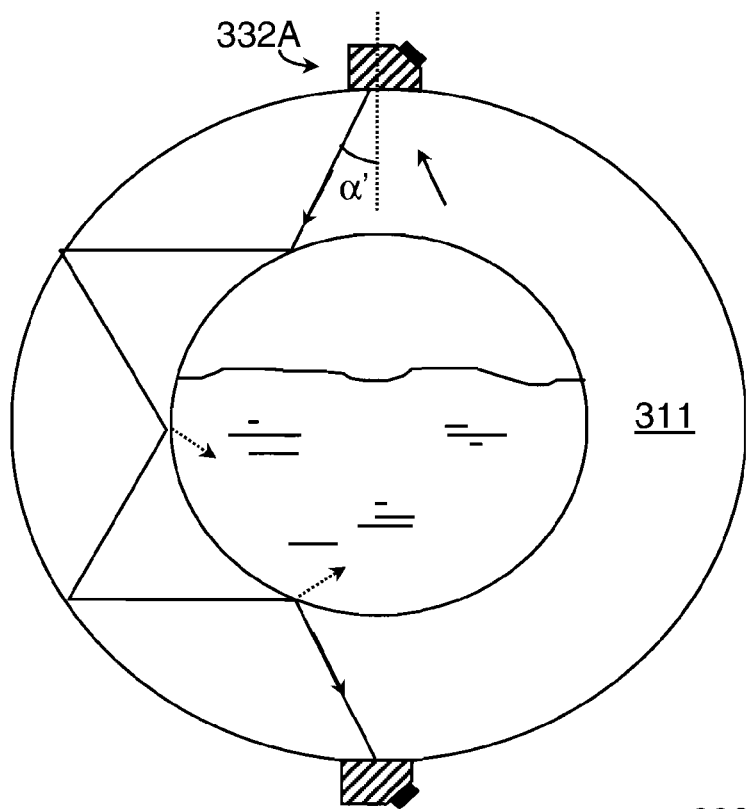
FIG. 3A shows a circumferentially oriented sensor based on circumferentially propagating shear waves for transmission analysis of a pipeline and/or flow analysis in the pipeline, in accordance with an embodiment of the present invention.
Figure 3B:
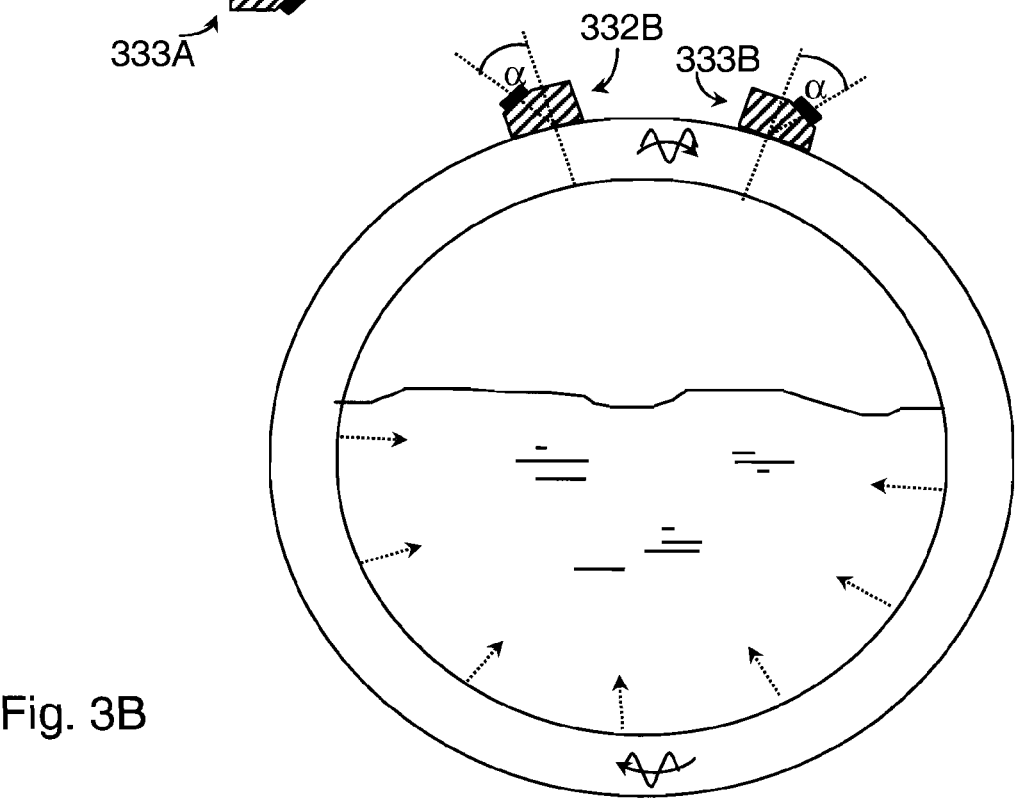
FIG. 3B shows a circumferentially oriented sensor based on circumferentially propagating Lamb waves for transmission analysis of a pipeline and/or flow analysis in the pipeline, in accordance with an embodiment of the present invention.

FIGS. 3A and 3B illustrate two examples of circumferentially oriented sensors for use in transmission analysis of a pipeline and/or flow analysis in the pipeline, in accordance with an embodiment of the present invention. FIG. 3A shows a circumferentially oriented sensor based on circumferentially propagating shear waves for transmission analysis of a pipeline and/or flow analysis in the pipeline, in accordance with an embodiment of the present invention. FIG. 3B shows a circumferentially oriented sensor based on circumferentially propagating Lamb waves for transmission analysis of a pipeline and/or flow analysis in the pipeline, in accordance with an embodiment of the present invention. In FIGS. 3A and 3B, the illustrated cross-sections are oriented perpendicular to the axis of the pipe to show how wave energy is radiated into the liquid phase of the fluid. In such aspects, above the gas/liquid interface the energy loss into the fluid becomes negligible.

The case of a circumferentially propagating shear wave is illustrated in FIG. 3A. A transmitter 332A and a receiver 333A of each channel are mounted on opposite sides of the pipe. The angle of incidence α may be set to 38 degrees; hence the receiver may be set to −38 degrees.

The case of a circumferentially propagating Lamb wave is illustrated in FIG. 3B. The transmitter and receiver of each channel are mounted close to each other, thus providing an almost complete round-trip for the wave. The angle of incidence α may be set to 70 degrees; hence the receiver may be set to −70 degrees. In general, the angle of incidence is chosen such that the refraction angle in the pipe wall may be larger than the critical angle and hence, a large fraction of the transmitted energy may be converted into a Lamb type wave. Similarly, the Lamb wave measurement may also be made along the axial direction of the pipe with the transmitter and receiver separated by a distance along said axial direction. Such measurement may be made at different circumferential positions, for instance, along the top side or the bottom side of the pipe, when the pipe is arranged in a horizontal type orientation.

A pulse-echo measurement by transmitting a compression wave or shear wave pulse perpendicularly into the pipe wall may also be used to measure the acoustic impedance of the material in contact with the inner pipe wall. Such a pulse transmitted perpendicularly into the pipe wall will reverberate between the inner and outer surfaces of the pipe wall. As such, by measuring the decay rate of the echoes generated by such reverberation, the acoustic impedance may be determined.

The type of the transmitter, i.e. compressional, shear or Lamb wave, and the angle of the incident beam into the pipe wall, α, may be selected so that different wave modes can be excited in the pipe wall. In certain aspects, the value of α may range from −90 degrees through 0 to +90 degrees, which may enables the generation and detection of various compressional, shear and Lamb modes and different direction of travel (clockwise or anti-clockwise) for different application requirements. The excitation waveform may be a pulse, (short) tone-burst or continuous wave. In many aspects of the present invention a pulse is the preferred waveform used for easy detection.

Both FIGS. 3A and 3B illustrate how, when the pipe is partly or fully filled with liquid, most of the propagating wave modes, referred to as leaky waves, leak energy into the liquid phase when traveling pass the section of the wall in contact with the liquid phase. Therefore the traveling waves are attenuated by the presence of the liquid phase in the pipe. For different wave modes, the expressions for the energy decay rate (also referred to as attenuation rate) in the pipe wall may be different and complex. For a given wave mode, however, the rate of attenuation, is a function of the acoustic impedance and the fraction (holdup) of the liquid phase in the pipe. This may be expressed as:

$$E = k\beta^x \quad (3)$$

where $\beta$ is the reflection coefficient of the liquid/pipe-wall interface which is determined by the liquid acoustic impedance, x is a function of the holdup H which is related to the liquid/pipe-wall interface length which the shear wave has traveled through, and k is a coefficient determined by the pipe geometries and the beam incidence angle. Both, $\beta$ and k may be determined by calibration measurements on the empty and completely filled pipe. With both parameters known, the output of the receiver can be directly converted into a measure of x and, hence, into a measure of the holdup H.

For the Lamb wave of FIG. 3B traveling around the pipe for more than a cycle, the RMS value of the first wave arrival, $E_1$, at a receiver 333B should be higher than that of the second arrival, $E_2$, one cycle later, due to the attenuation effect. The ratio $E_2/E_1$, which represents the attenuation rate, may be approximately expressed by:

$$E_2/E_1 = k\beta^x \quad (4)$$

Figure 4:
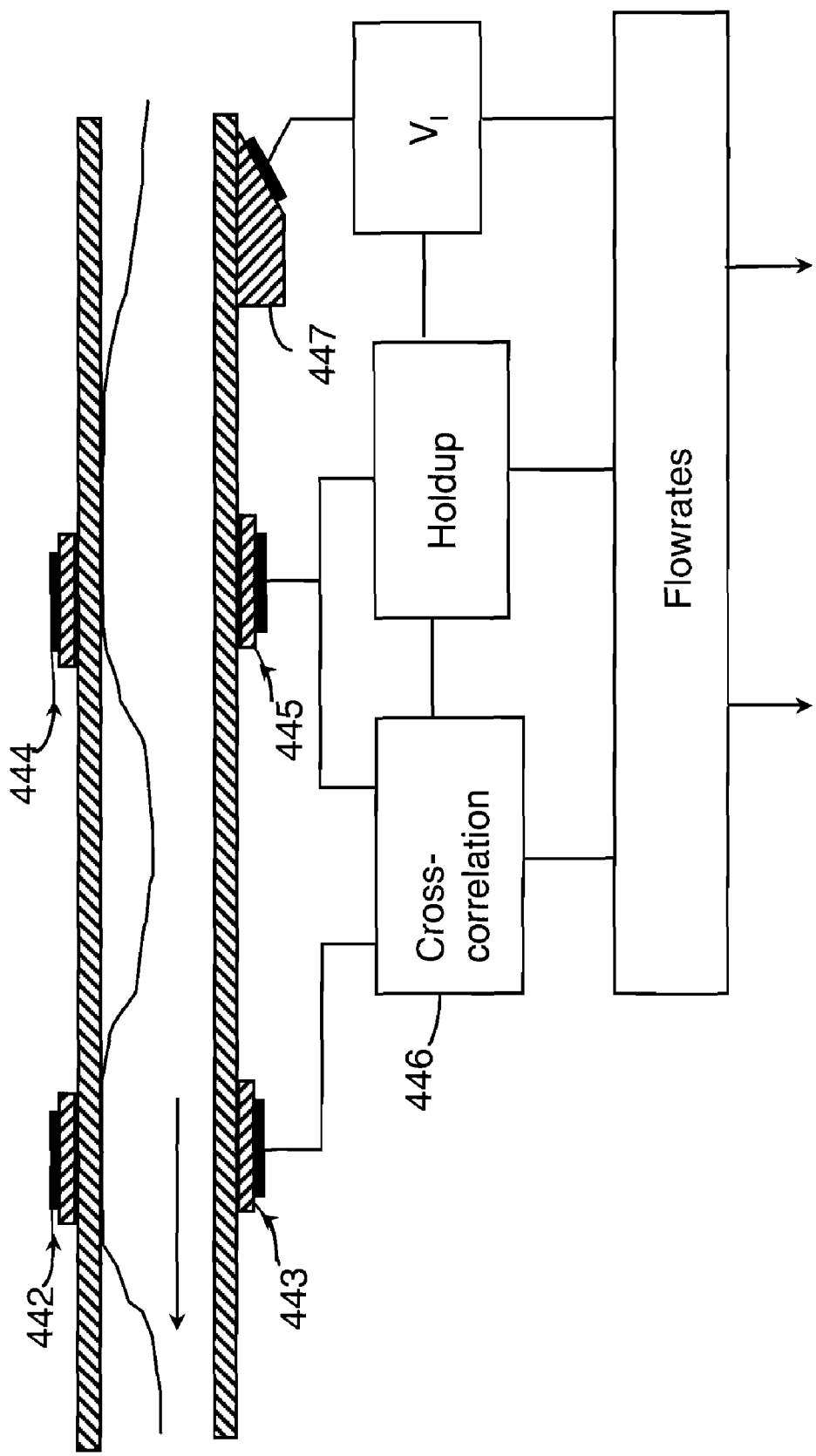
FIG. 4 shows two clamp-on ultrasonic measurement channels for flow assurance based on the principles of leaky wave modes, as described above, in accordance with an embodiment of the present invention.

FIG. 4 shows two clamp-on ultrasonic measurement channels for flow assurance based on the principles of leaky wave modes, as described above, in accordance with an embodiment of the present invention. In certain aspects, the channels may be axially separated by a distance d of the order of 100s of millimeters and usually chosen to lie within a range of 1 to 10 times of the pipe diameter. Each of the channels may consist of one transceiver 442 and 444, respectively, and one receiver 443 and 445, respectively. In an embodiment of the present invention, the transmitters and receivers may be operated in a range around 0.5 MHz.

Dynamic fluctuations of the energy attenuation measured by the two channels may be processed by a cross-correlator 46 to produce a time-of-flight measurement. The known separation between the transmitters and receivers and the measured time delay may be processed in the following equation to calculate the flow velocity of the mixture in the pipeline:

$$V_f = d/\tau \quad (5)$$

where d=the separation between the transmitters and receivers and $\tau$=the measured time delay.

This measured velocity, $V_f$, may be interpreted by using appropriate flow models to produce the mixture or homogeneous velocity of the flow, $V_h$. Appropriate flow models are may be known in the art. Examples of such models may be found in Dukler, A. E. and Hubbard, M. G. "A model for gas liquid slug flow in horizontal and near horizontal tubes", Ind. Eng. Chem. Fundam. 14 pp. 337-347 (1975) and in Nicholson, M. K., Aziz, K. and Gregory, G. A., "Intermittent two phase flow in horizontal pipes: predictive models", Can. J. Chem. Eng. 56 pp. 653-663 (1978), the entire contents of both references are hereby incorporated by reference.

A Doppler sensor 447, which in certain aspects may be an angled shear wave probe, may be mounted on the bottom side of the pipe. For some applications of an embodiment of the present invention, it may be advantageous to add a second Doppler probe to the top side of the pipe. Doppler frequency shifts produced by gas bubbles and solids particles in the liquid phase may provide information on the velocity of the liquid phase, $V_l$.

In an embodiment of the present invention, the fraction or holdup of the liquid phase, $H_l$, in a gas/liquid flow, may be measured by the Lamb wave method shown in FIG. 3B and by using equation (4). In another embodiment of the present invention, $H_l$ may be measured by one or multiple ultrasonic Doppler sensors installed at different positions around the pipe circumference. These Doppler sensors detect the location of the main gas liquid interface that separates the liquid and gas phases in the pipe because such an interface produces strongest Doppler echo signal. The liquid holdup is calculated from the geometry defined by the gas/liquid interface.

In an embodiment of the present invention, flow rates of individual phases may be derived from the three measurements discussed above using the following equations:

$$Q_l = AH_l V_l \quad (6)$$

and $$Q_g = A(V_h - H_l V_l) \quad (7)$$

where A is the cross-sectional area of the pipe bore.

In alternative embodiment, the two measured parameters, $V_l$ and $H_l$ may be combined with a slip model to give $Q_l$ and $Q_g$. The slip model provides the differential or slip velocity $V_S$ between the liquid and the gas, and, hence, enables the gas velocity $V_g$ to be determined from the following relationship:

$$V_g = V_s + V_l \quad (8)$$

where $V_s$ is the slip velocity. The flow rate for the gas flow can then be determined by replacing equation [6] with:

$$Q_g = A(1 - H_l) V_g \quad (9)$$

Figure 5:
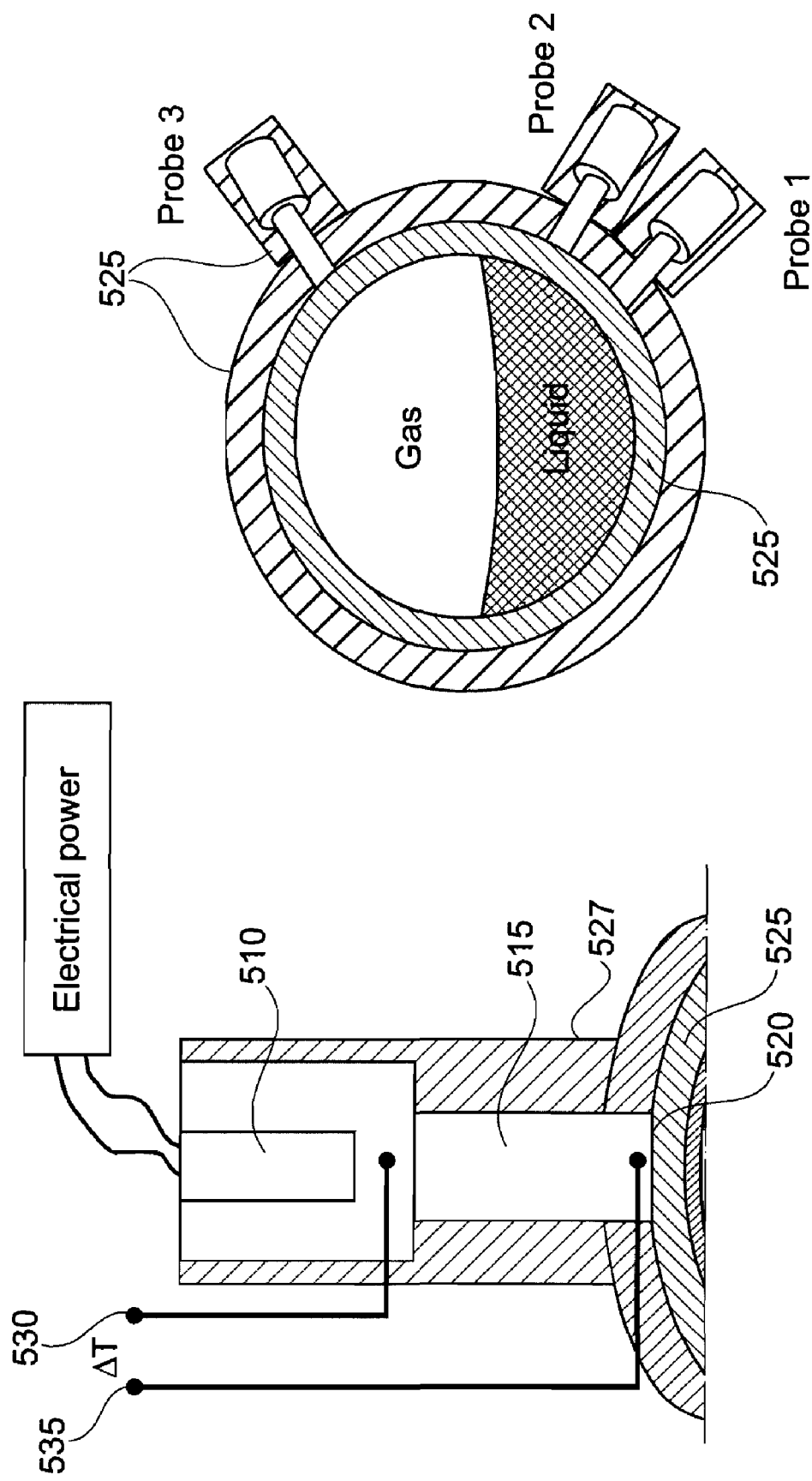
FIG. 5 illustrates a non-invasive thermal probe for use in a flow assurance system, in accordance with an embodiment of the present invention.

FIG. 5 illustrates a non-invasive thermal probe for use in a flow assurance system, in accordance with an embodiment of the present invention. In embodiments of the present invention, a given heating or cooling power/energy may be applied to a heater/cooler 510 that may be embedded in one end of a metal probe body 515. At the other end of the probe, a sensing tip 520 may be positioned to be in contact with a pipe wall 525. The temperature (T2) at the heater/cooler end of the probe may depend mainly on the applied power level. The temperature (T1) at the sensing tip 520 may be sensitive to the heat flow between the probe and the pipe.

In certain embodiments, thermal insulation 527 may be applied to the pipe and to the probe to provide that the heat flow from the probe into the pipe is proportional to the differential temperature, $\Delta T = T2 - T1$. The differential temperature may be measured in an embodiment of the present invention by a source thermocouple 530 and a pipe wall thermocouple 535. Apart from the effect of fluid temperature ($T_f$), the temperature of the mixture in the pipeline, which may in certain aspects be measured by the thermo probe before power is applied, $\Delta T$ or the heat flow depends on the flow condition and the properties of the fluids in the pipe.

More specifically, given the value of $T_f$, the value $\Delta T$ depends on the thermal conductivity of the fluid as well as the Prandtl number and the Reynolds number of the fluid flow. In the absence of the scale deposition on the wall, $\Delta T$ provides an indication of the fluid type, i.e. water, oil or gas, if the flow velocity and the flow regime are known. In the case of scale deposition, in accordance with an embodiment of the present invention, $\Delta T$ may be processed with knowledge of the scale, such as scale thickness, scale type and or the like to determine fluid properties because the convection effect of the fluid in the pipe on the heated pipe wall may affected by the scale. Moreover, in some embodiments of the present invention, with knowledge of the flow in the pipe, the $\Delta T$ may be processed to make determinations about any scale on the pipe wall.

FIG. 6 illustrates an embodiment of a flow assurance pipeline monitoring system comprising multiple sensors, in accordance with an embodiment of the present invention. In the illustrated embodiment, data may be acquired by multiple non-invasive sensors 601 *a-e*. Each of the non-invasive sensors may operate in different modalities. Merely by way of example, in certain aspects, a range-gated ultrasonic Doppler sensors 601*a* or a plurality of the range-gated ultrasonic Doppler sensors 601*a* may used for determining scale properties and/or flow properties in the flow assurance/pipeline monitoring system in accordance with an embodiment of the current invention. In another example, a non-invasive thermal probe sensor 601*b* or a plurality of non-invasive thermal probe sensors 601*b* may used for determining scale properties and/or flow properties in the flow assurance/pipeline monitoring system in accordance with an embodiment of the current invention.

In a further example, an acoustic impedance sensor 601*c* or a plurality of acoustic impedance sensors 601*c*—which may comprise a pulse-echo type sensor or sensors 601*c-pe* and/or a Lamb wave type sensor or sensors 601*c-lwp*—may be used for sensing scale and/or flow properties in the flow assurance/pipeline monitoring system in accordance with an embodiment of the current invention. In yet further examples, a combination of one or more of at least one of each of the different sensors may be configured in a flow assurance/pipeline monitoring system in accordance with an embodiment of the current invention.

The operation and processing of outputs from such sensors in accordance with embodiments of the present invention are disclosed above. In different embodiments of the present invention, different combinations of the non-invasive sensors 601 may be used. Merely by way of example, in some embodiments only a plurality of the non-invasive sensors 601*a* may be used in other embodiments the non-invasive sensors 601*a* may be used in combination with the non-invasive sensors 601*b*, etc.

Figure 6A:
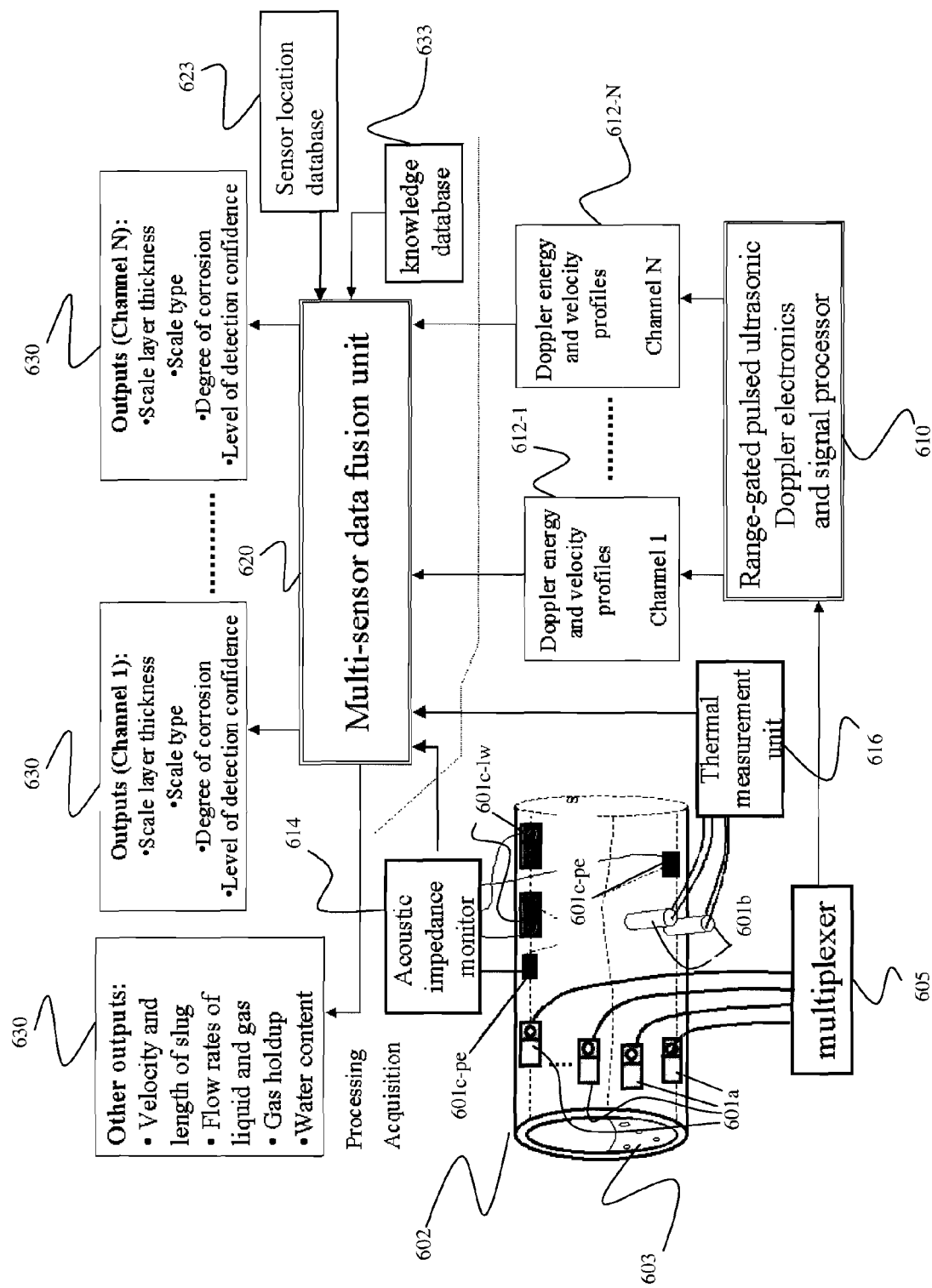
FIG. 6A illustrates an embodiment of a flow assurance pipeline monitoring system comprising multiple sensors, in accordance with an embodiment of the present invention.
Figure 6B:
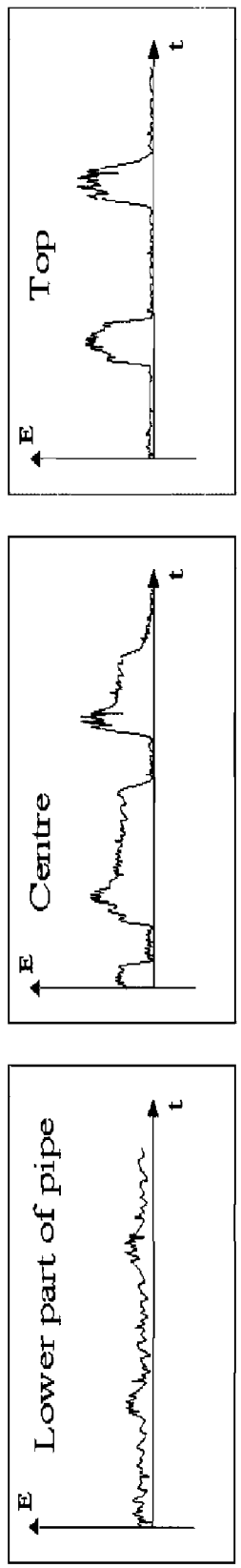
FIG. 6 B illustrates time series signals of depth-averaged Doppler energy (upper) and velocity (lower) signals for three transceivers mounted near the bottom (left figure), middle (centre) and top (right) of the pipe.
FIG. 6C illustrates a comparison of a measured Doppler profile with a stored/reference Doppler profile, in accordance with an embodiment of the present invention.
FIG. 6D illustrates how input data to a second level data fusion process may be mapped to output determinations, in accordance with an embodiment of the present invention.
Figure 6B:
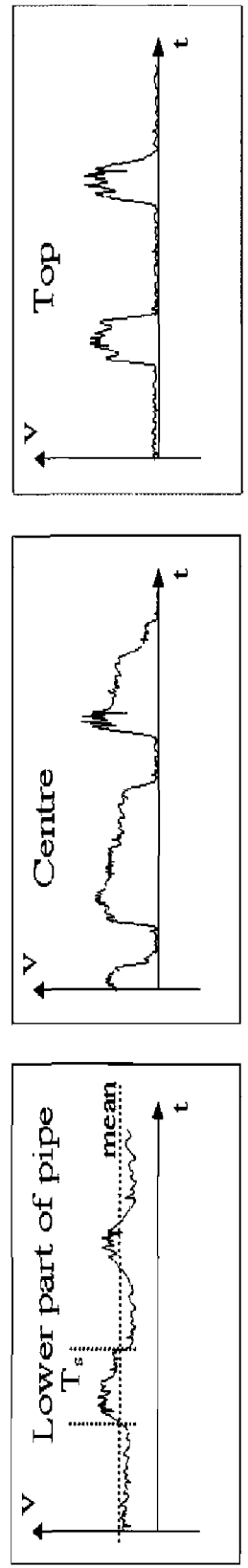

In FIG. 6A, a more or less horizontal pipe 600 is shown carrying a gas/liquid multiphase flow 603. The multi-sensor system in accordance with an embodiment of the present invention may consist of at least one range-gated ultrasonic Doppler sensor. In certain aspects, a plurality of the range-gated ultrasonic Doppler sensors may be clamped at different circumferential positions of the pipe exterior. For a horizontal pipe, one or more of the range-gated ultrasonic Doppler sensors may be positioned close to the bottom, centre and top portions of the outer circumference of the pipe. In one embodiment of the present invention, in addition to the range-gated ultrasonic Doppler sensors, at least one acoustic impedance sensor may be clamped onto the pipeline section. In certain aspects, a plurality of the acoustic impedance sensors may be coupled with the pipeline at various locations around the circumference of the pipe. The acoustic impedance sensors may be disposed at different circumferential positions of the pipe exterior. For a horizontal pipe, the acoustic impedance sensors may be disposed around the outer surface of the pipe at the same circumferential height(s) as a nearby Doppler probe.

In certain embodiments, the acoustic impedance sensors may be configured to provide for diversity in the mode of impedance measurements. Merely by way of example, acoustic impedance may be measured with two frequencies with a first acoustic impedance being measured at a first frequency with the acoustic impedance sensor operating in a pulse-echo mode and a second acoustic impedance being measured at a separate frequency with the acoustic impedance sensor operating in a Lamb wave mode.

In further embodiments of the present invention, the flow assurance/pipe monitoring system may include at least one non-invasive thermal probe sensor. The non-invasive thermal probe sensors may be used in combination with the range-gated ultrasonic Doppler sensors and/or the acoustic impedance sensors. In embodiments utilizing a plurality of the non-invasive thermal probe sensors, each of the non-invasive thermal probe sensors may be clamped at different circumferential positions with the pipe exterior. In certain aspects, for flow assurance and/or pipe monitoring of a horizontal pipe, the non-invasive thermal probe sensors may be disposed at the same circumferential height as a nearby range-gated ultrasonic Doppler transceiver sensors and/or acoustic impedance sensor.

The sensors listed above are non-limiting, and in other embodiments additional types of sensors based on other measurement principles, either invasive or non-invasive, may be added to the open system structure. Merely by way of example, invasive and/or noninvasive flow meters, invasive and/or noninvasive density meters, invasive and/or non-invasive sampling systems and/or the like may be used with one or more of the sensors of the sensor configurations discussed above In certain aspects of the present invention, a plurality of the clamp range-gated ultrasonic Doppler transceiver sensors may be clamped onto the pipe section and positioned to address the pipe to provide for generation of a shear wave in the pipe wall 602. The angle of address in certain aspects may be in an incident angle range of 15 to 85 degrees, where a perpendicular incident angle is 0 degrees. The transceiver may comprise a narrow band transducer and it may have, for example, a centre frequency within a range of 1 to 10 MHz. In one embodiment, range-gated ultrasonic Doppler measurements from a corresponding range-gated ultrasonic Doppler transceiver probe at each of the positions may be performed by connecting the corresponding transceiver to the pulsed Doppler electronics and signal processor through a multiplexer 605.

Merely by way of example, the multiplexer 605 may be first coupled with a range-gated ultrasonic Doppler transceiver sensors at the lowest circumferential position, and then acquires data for a period of T, producing a number of M Doppler velocity profiles and M energy level profiles, say M=60 or 600. Each of these profiles may contain data corresponding to a depth range that starts from inside the pipe wall 602 and ends some distance into the mixture flow. In certain aspects, a Doppler electronics and signal pre-processor 610 may process each point in the velocity profiles that may be obtained from the average frequency shift of the Doppler signal within the corresponding depth range gate. Each point in the energy level profile may be calculated from the area under the frequency spectrum of the Doppler signal within the corresponding range gate.

The energy profile is important because it tells the concentration of the reflectors in the flow and, thus the reliability of a Doppler velocity estimation. After finishing acquisition on one range-gated ultrasonic Doppler transceiver sensors, the multiplexer 605 then switches to the next one, and the same acquisitions are carried out. In aspects of the present invention, this multiplexing or probe-scan continues until data at the last transceiver probe are acquired. In some aspects, this complete scanning process may repeat at regular update intervals. In certain embodiments, the two types of output profiles, namely velocity and energy for each of the N range-gated ultrasonic Doppler transceiver sensors, may be provided as an output 612-1 through 612-N to a data fusion processor 620.

As discussed above, the acoustic impedance sensors may measure the energy attenuation of a certain wave mode in the pipe wall 602 and correlate such attenuation with the impedance of the material in contact with the pipe wall. In certain embodiments of the present invention, more than one mode of the impedance measurement may be utilized to provide for more accurate and/or robust flow assurance and/or pipeline monitoring. Merely by way of example, the acoustic impedance sensors may be configured to operate in one or both of Lamb wave and pulse-echo compression wave modes.

In an embodiment of the present invention, an acoustic impedance monitor 614 may receive one or more outputs from one or more of the acoustic impedance sensors. Similarly, a thermal measurement unit 616 may receive one or more outputs from one or more of the non-invasive thermal probe sensors. The acoustic impedance monitor 614, the thermal measurement unit 616, and/or the Doppler electronics and signal pre-processor 610 may provide processed versions of the outputs from one or more of the sensors to the data fusion processor 620.

As such, in some embodiments of the present invention, data from multiple sensors is first fed to three pre-processors, referred to as first-level data fusion processors (the acoustic impedance monitor 614, the thermal measurement unit 616, and/or the Doppler electronics and signal pre-processor 610) to prepare them into forms suitable for further processing in the data fusion processor 620. The Doppler pre-processor 610 may input into the data fusion processor 620 the real-time velocity and energy profiles of the N transceiver probes from the Doppler signal processor output. By processing this Doppler data with data regarding location of each of the different sensors—the sensor position data may be stored in a memory 623, which may be a database or the like, that may be coupled with the data fusion processor 620—the data fusion processor 620 may produce real-time flow velocity and holdup signals for each sensing location.

In an embodiment of the present invention, the real-time flow velocity and holdup signals for each sensing location may be used by the three pre-processors (the acoustic impedance monitor 614, the thermal measurement unit 616, and/or the Doppler electronics and signal pre-processor 610) to select the most relevant time periods during which time-averaged Doppler profiles, acoustic impedance and heat dissipation data may be obtained. In certain aspects, the Doppler pre-processor 610 may produce, for each Doppler sensor position, time-averaged velocity profiles and the corresponding flow conditions/regimes under which the profiles are obtained. This data may be sent to the data fusion processor 620 for further processing. The Doppler pre-processor 610 may also produce outputs such as liquid flow rates, liquid/gas holdup, average liquid velocity, slugging parameters (velocity, length of liquid slugs, etc.) and/or the like.

The data fusion processor 620 may combines the different input data, such as the effective wall thickness changes measured by the multi-probe Doppler system, the flow regime data, sensor positions, the processed acoustic impedance and the heat dissipation data, to determine the conditions of the pipe and the flow of a mixture through the pipe. Any a priori knowledge of the flow or fluids obtained by other means, such as fluid properties from samples, history of production (i.e. water breakthrough), geology data, predictive models, etc. may also be stored on a memory 633 and may be used as inputs to the data fusion system. A series of outputs 630 processed by the data fusion processor 620 may include, a scale layer thickness around the pipe, an approximate scale type, a degree of corrosion, fluid properties inside the pipe such as acoustic impedance and thermal conductivity, and also inferred water content in the liquid, all with corresponding detection confidence levels. The series of outputs 630 may be displayed, output to further processors, output to a system managing the pipeline and/or the like.

In an embodiment of the present invention, the Doppler pre-processor 610 may take the consecutive sequences of Doppler velocity and energy profiles for a number of N range-gated ultrasonic Doppler transceiver sensors as an input. In different aspects of the present invention, the Doppler pre-processor 610 may carry out the following types of processing:

For each range-gated ultrasonic Doppler transceiver sensors, the time series of Doppler energy and/or velocity may be produced. For instance, instantaneous Doppler energy and velocity profiles can be acquired at a series of time points, $t_1$, $t_2, \ldots t_n$. For a horizontal slug flow, these profiles may vary significantly at different time points. For instance, time point $t_1$ may correspond to a stratified gas/liquid section of the flow and $t_n$ to the liquid slug section passing the sensor. By averaging each instantaneous profile along the depth axis, one velocity and/or energy point may be obtained for each time point, e.g. $t_1$ or $t_n$. As such, time series such as those shown below may be obtained. The diagrams below, shows the typical time series of three probes mounted at different circumferential positions on a horizontal pipe conveying a gas/liquid slug flow.

FIG. 6 B illustrates time series signals of depth-averaged Doppler energy (upper) and velocity (lower) signals for three transceivers mounted near the bottom (left figure), middle (centre) and top (right) of the pipe.

With the help of the sensor position data, the Doppler pre-processor 610 may combines profiles from all the distributed range-gated ultrasonic Doppler transceiver sensors to produce estimates for liquid flow velocity, flow rates, phase fraction, slug parameters and/or the like. The velocity and length of the liquid slugs may be measured from signals such as those shown in the time series above.

The Doppler pre-processor 610 may identify flow regimes from the signature of the time series shown above. The Doppler pre-processor 610 may also produces descriptive parameters for each flow regime, such as the mean value and the variance of liquid velocity, reflector concentration in the liquid phase, gas fraction, etc.

The Doppler pre-processor 610 may produce new Doppler velocity/energy profiles from segments of the time series illustrated above, such processing being termed data segmentation. For instance, the slug sections may be identified in the time series shown above, because the slug sections may contain a higher concentration of reflectors. Therefore, by selecting only the Doppler velocity profiles acquired during the slug intervals, such as $T_s$, for deposition and corrosion detection, the signal to noise ratio of the Doppler measurement may be improved. The output profiles produced by the pre-processors are not necessarily limited to the velocity or energy profiles. Various data transformations may be applied to the original profiles to translate them into ones with easily identifiable features, such as a peak showing the boundary of the flow/non-flow zones. Methods such as logarithmic operation, derivation, wavelet transform, to name a few, can be used. Therefore the word "profile" used here means broadly the distribution of certain characteristic number versus depth.

Doppler pre-processor 610 may provide for updating reference profiles and producing current and historical measurements of effective wall thickness. A reference profile may be used to measure the relative change of the zero-velocity zone on the Doppler profile. Originally the first reference may be obtained in a calibration run, for instance, after the monitoring system is first installed, when the pipe condition is considered as good, when the pipe section has been evaluated and a known scale deposit recorded and/or the like. Any pipe condition change after this baseline, which may be caused by corrosion, deposition on the wall and/or the like, may be calculated in an embodiment of the present invention from the difference between the currently measured profile and the reference one.

Figure 6C:
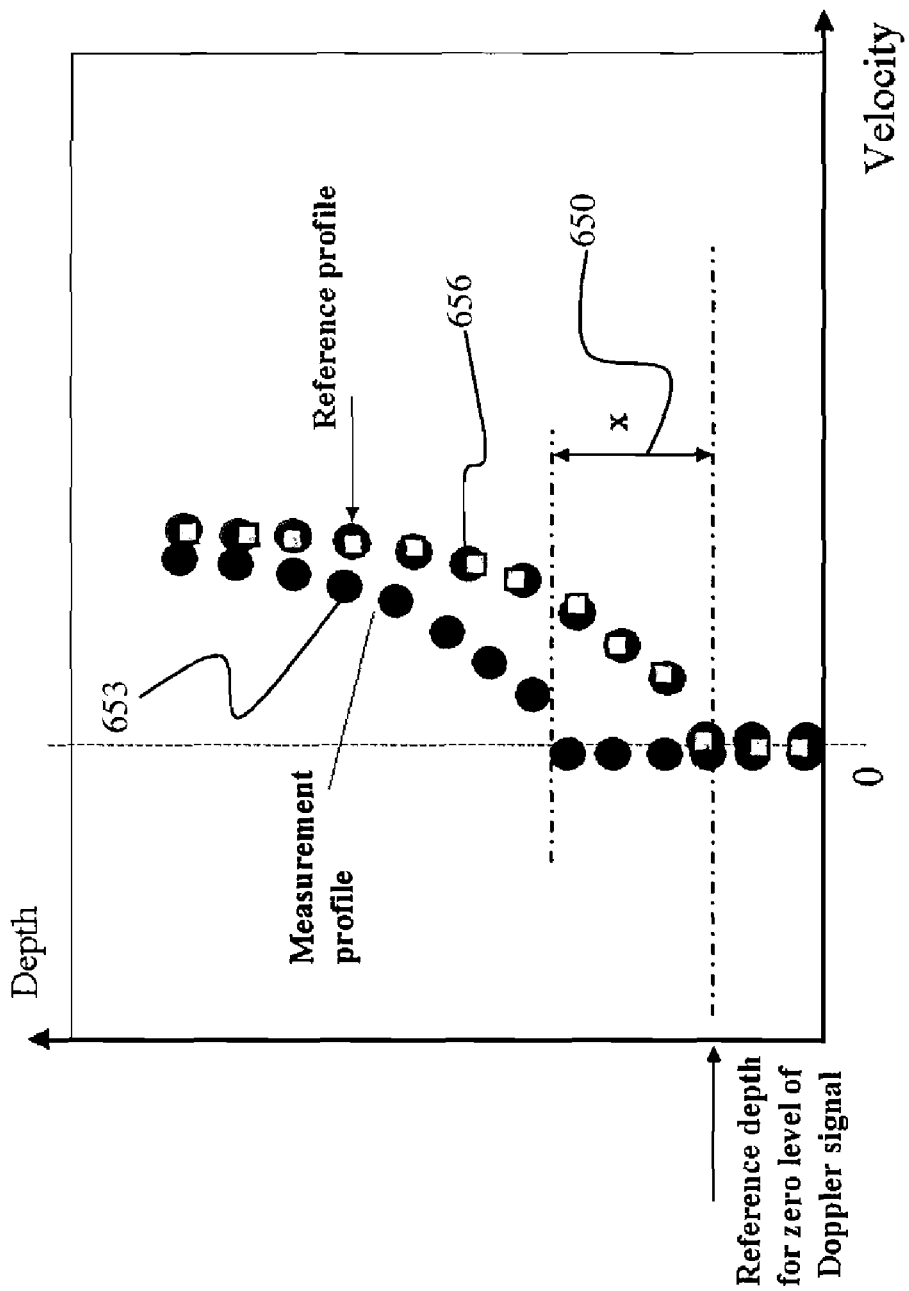

FIG. 6C illustrates a comparison of a measured Doppler profile with a stored/reference Doppler profile, in accordance with an embodiment of the present invention. As shown in the illustration a section x 650 between a measured Doppler profile 653 and a reference Doppler profile 656, may provide the thickness of the scale deposit. In the case of corrosion, the zero-velocity section on the measured profile should be shorter than that on the reference profile 656, and a negative value for the section x 650 will be obtained. However, the velocity/energy profiles, or their transformations, sometimes change with the flow regime. For instance, when the flow slows down, the zero-velocity section on the Doppler velocity profile may increase because of reduced reflector concentration near the pipe wall.

In order to reliably monitor solid deposition, a new reference profile is always produced whenever a significant change in flow regime is detected. This new reference is used to detect subsequent changes in effective pipe wall thickness. As a result, the pre-processor produces multiple reference profiles, a sequence of measured wall thickness changes with respect to the current and the historic references. This method of deriving the thickness change from two profiles obtained at different times is an example of data fusion applied to measurements diversified in time domain.

FIG. 6C shows how in certain aspects determining the change in pipe wall thickness—which may be due to deposit build up, corrosion or the like—may be provided by comparing a currently measured Doppler velocity profile, a transformed Doppler profile and/or the like with a reference profile.

In certain aspects, the processed Doppler profiles and thickness measurements with respect to the current and the historic reference profiles may be obtained for all the (N) transceiver probes. All the data are then sent to the data fusion processor 620 for further processing. The time series may also be used to select acoustic impedance data and thermal sensor data from the acoustic impedance monitor 614 and the thermal measurement unit 616, respectively, that corresponds to different flow sections. Merely by way of example, for scale deposit detection, the contrast between the acoustic impedance of the scale and that of the fluid in contact with the wall may be processed. In certain aspects where an impedance sensor is disposed on the upper part of a horizontal pipe conveying a gas/liquid slug flow, the measurement data corresponding to the stratified gas section that frequently passes the pipe across-section may be selected for processing because such a gas section may have an acoustic impedance that is much lower than that of scale, and therefore the scale is easier to detect with a gas background.

In embodiments of the present invention, as with the Doppler pre-processing, dynamic updating of measurement references may be performed in the impedance and thermal preprocessors. For instance the heat loss measurement may be strongly dependent on the flow velocity as a result of forced-convection by the fluid. Therefore, if there is a significant change in the velocity of the mixture in the pipe, which velocity change may be determined by the Doppler system, then when the Doppler pre-processor determines such a velocity change or a lack of such a change a new reference thermal measurement may be taken. Heat-loss variations relative to the new and historical references may be sent to the second level data fusion processor for further processing.

In an embodiment of the present invention, the first level data fusion or pre-processing may generate the data that may be directly used to show some abnormal conditions under some flow regimes. For instance, for a near horizontal gas/liquid slug flow, the effective wall thickness change, due to solid deposition, corrosion and/or the like may be shown by Doppler measurements at or around the middle height position of the pipe—where the large fluctuating gas/liquid interface may produces strong Doppler signals. However, for some other flow regimes, or for detection of some other parameters, such as the deposition type, water content in oil or the like, processing of data from Doppler sensors, impedance sensors and/or thermal sensors in a second level data fusion processor may be performed. For example, a combination of data from Doppler sensors with measurements from different sensors may provide for correcting scale thickness measurement errors or the like that may be due to the effect of the sound velocity in the scale layer.

In certain aspects, as an alternative to implementing both the first and the second level data fusion processing on the same hardware processor, the second level data fusion processing software may be implemented on a physically separate or remote hardware processor located away from the sensors, e.g. a computer located in a central control room. The first task of the second level processing may be to determine what flow regime is in existence inside the pipe. In one embodiment, this type of analysis may be processed/performed by combining flow regime related parameters produced by the Doppler pre-processor with background knowledge of the pipe layout, e.g. vertical pipe layout in sensing zone, horizontal pipe layout in the sensing zone or angle of inclination of the pipe in the sensing zone. In an embodiment of the present invention, when a certain flow regime is determined, a certain fusion process, which is specific to that regime, may be selected to process desired output parameters. In this way, in an embodiment of the present invention, the flow assurance/pipeline monitoring system may intelligently deduce in real-time when to sense certain properties depending upon the flow regime existing in the pipe. For example, Doppler sensing of deposits depth on the pipe by the range-gated ultrasonic Doppler transceiver sensors may not be performed when there is a single-phase gas flow in the pipe or zero-velocity/very-slow mixture flow detected in the pipe.

In an embodiment of the present invention, flow assurance/pipeline monitoring of a pipe may be made for near horizontal gas/liquid flows in the pipe. The inputs for data fusion may be the relative wall thickness changes in the deposits on the pipe wall measured by the multiple Doppler transceiver sensors—which may comprise N inputs from N range-gated ultrasonic Doppler transceiver sensors—the inputs from n multiple acoustic impedance measurements and/or thermal measurements from m thermal probes, where each of the individual sensors may be disposed around the pipe circumference. Also available for data fusion may be flow regime related parameters, that may be determined from one or more sets of the sensors in an initial data fusion, corresponding to each sensor position, which may include the flow velocity, the reflector concentration, the phase (e.g. liquid or gas) in contact with the pipe and/or the like.

The sensor position data and any other knowledge about the pipeline and fluid properties are also useful inputs. The output mapping scenario below shows how input data to the second level data fusion may be mapped to output determinations.

Figure 6D:
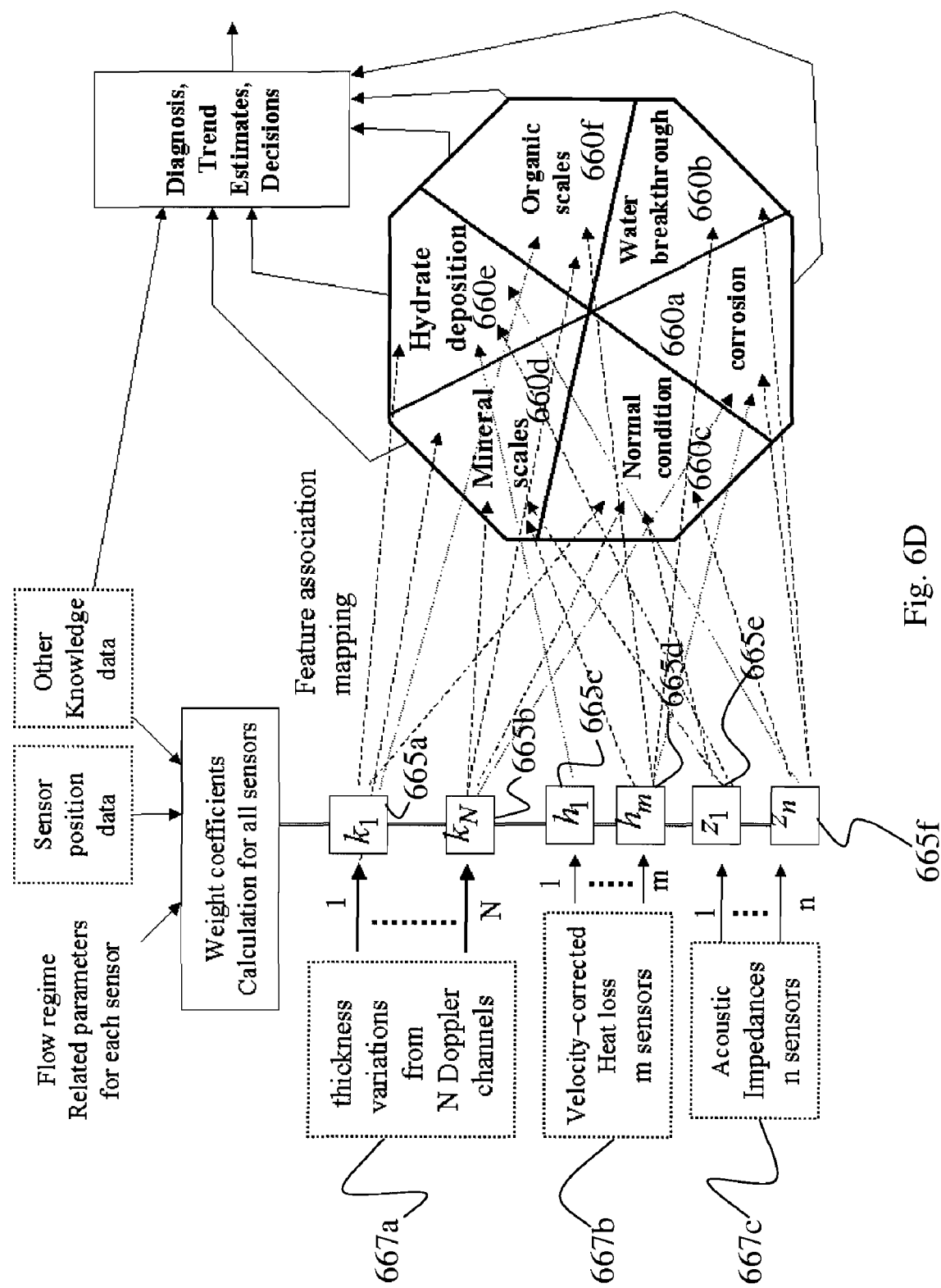

FIG. 6D illustrates how input data to a second level data fusion process may be mapped to output determinations, in accordance with an embodiment of the present invention. In such mapping and the like, sensor position data and any other knowledge about the pipeline and fluid properties may be useful inputs. In the data mapping illustrated in FIG. 6D, six main scenarios 660a, 660b, 660c, 660d, 660e and 660f are depicted, some of the scenarios are mutually exclusive, but some may be overlapping—such as corrosion 660a and water breakthrough 660b. In an embodiment of the present invention, the data fusion process may map input measurements 665a-f from one or more sensors 667a-c onto a scenario space of the six main scenarios 660a, 660b, 660c, 660d, 660e and 660f or the like. This scenario mapping may involve deciding which ones of the inputs are the symptoms of a scenario and how much weight a symptom has on its diagnosis. In certain aspects, experimental and theoretical correlations between the symptom and the diagnosis and/or various inference methods between the symptom and the diagnosis—such as Bayesian inference, Kalman inference and/or the like—may be used.

In certain aspects, filtering, Dempster-Schafer theory, neural network, fuzzy logic and even a weighted voting, may help to form an estimation/decision/determination in the second level data fusing process. In the data mapping/data fusion shown above, weighted voting data fusion, in accordance with an embodiment of the present invention, data input may be mapped to the processed pipeline scenario. In such a data fusion process, a weighting coefficient vector is generated for each measurement input (symptom). The number of elements in the vector equals the number of scenarios. For instance, $k_1$ is generated for the first Doppler channel and it has six elements corresponding to the six scenarios show in the data mapping above. The weighting coefficients are determined from the correlations between the symptom and the scenario, which may be obtained by experiments and/or modeling. The coefficients are also affected by the fluid regime related data, sensor position data as well as relevant information shown as the "other knowledge data". For instance, in certain aspects of the present invention, if the signal to noise ratio at the Doppler transceiver mounted near the lowest part of the pipe circumference is poor, then a small weighting value may be used to make the influence of this unreliable measurement insignificant.

In an embodiment of the present invention, a diagnosis may be formed on the result of such a data fusion weighted voting process. Merely by way of example, if the heat losses from the thermal probe sensors around the pipe reduce significantly, i.e. temperatures rise significantly, this may provide a strong indication of an organic deposition occurring on the pipe wall. The evidence may be further strengthened if a wall thickness increase is measured by the Doppler sensors and/or by a small increase in the measured impedance value, since in case of a mineral scale the impedance will be much higher. As such by data fusion of outputs from a plurality of different sensors more and better analysis of flow and/or pipeline condition may be provided.

In certain embodiments of the present invention, a dynamic data fusion process may be used, wherein the inputs and/or outputs from the second level data fusion processor may be updated repeatedly. Merely by way of example, confidence/ability/accuracy of diagnosing properties of deposits on the pipeline may increases when multiple symptoms of the deposit, such as the thickness of the deposit layer, the acoustic impedance caused by the deposited layer and/or the pipe wall temperature, increase with time. In an aspect of the present invention, the voting results for all the likely scenarios may be compared in the second level data fusion process and the most likely scenarios regarding flow and/or pipe condition may be processed by a decisions/trend unit associated with or incorporated in the data fusion processor. Such a decisions/trend unit or an associated processor receiving outputs from the decisions/trend unit may also predict further development of the scenario and suggest decisions for remedial measures.

Figure 7:
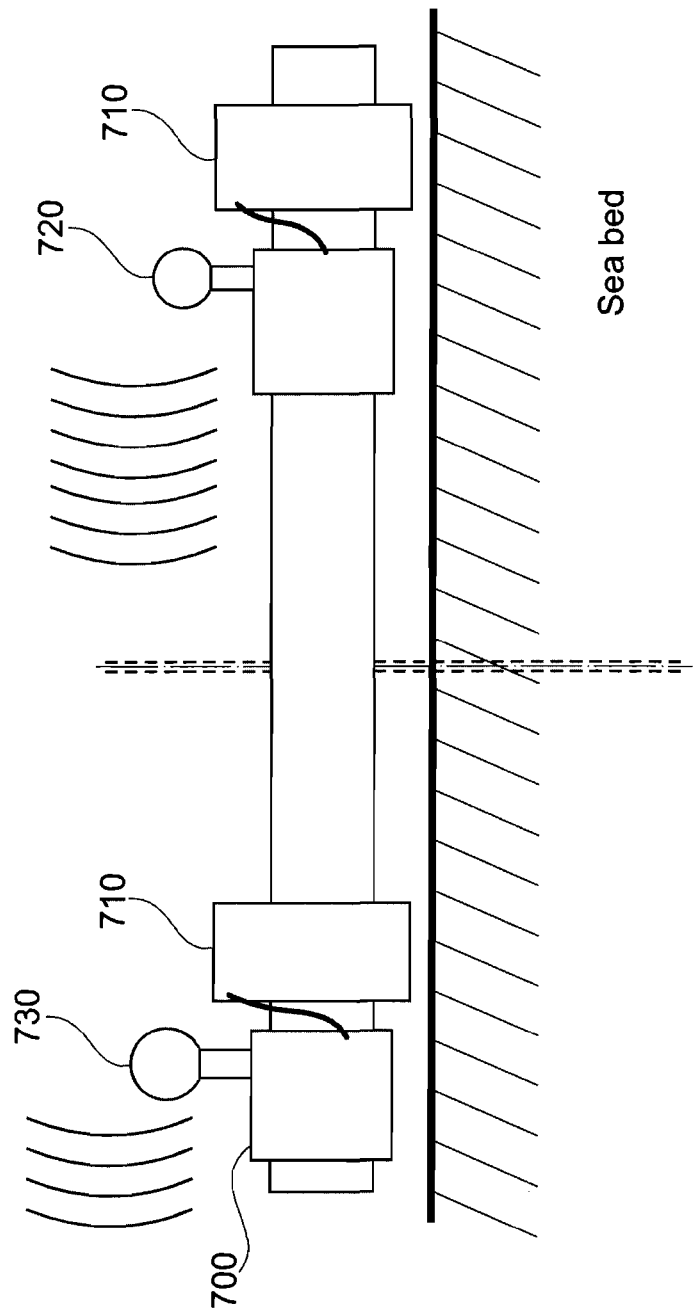
FIG. 7 illustrates sensors of a flow assurance and/or pipeline monitoring system configured in a distributed monitoring network on a pipeline to provide for power supply to the sensors and communication between the sensors and data processing units, in accordance with an embodiment of the present invention.

FIG. 7 illustrates sensors of a flow assurance and/or pipeline monitoring system configured in a distributed monitoring network on a pipeline to provide for power supply to the sensors and communication between the sensors and data processing units, in accordance with an embodiment of the present invention. Since the sensors may be located far away from the sub-sea power and telemetry hub, cable connection to them may not be available. FIG. 7 shows an arrangement of distributed sensors 700 powered by locally installed energy harvesting systems 710, and networked through wireless links comprising a wireless transmitter 720 and a wireless receiver 730. In certain aspect, the wireless links may be acoustic links. In other aspects, wireless network technology, such as wireless electromagnetic links or the like may be used.

In various embodiments of the present invention, various energy harvesting systems, such as system based on pressure, mixture flow, thermal-electric principles and/or the like may be used. In some aspects, energy may be sent along or to the sensor network. For example, transducers may be used on the network and energy such as pressure waves or the like may be sent to the transducer for conversion and supply to the sensor. A thermal-electric based generator may be used in the network system, where the thermal-electric based generator may utilize a significant temperature difference between the warm fluid inside the pipe and the cold sea-water outside to generate/harvest energy. Power may be generated by the energy harvesting systems 710 and in certain aspects may be accumulated in suitable storage devices, e.g. supper-capacitors or the like, for use when required. This energy stored/harvested energy may be applied to the sensor system during required data acquisition and telemetry periods.

A data transfer link, such as an acoustic sonar link, wireless link or the like may be used to transmit acquired data. The longer the transmission distances, the higher the power requirement. As such in certain aspects, for long distance transmission, short hop relay may be used. In such a configuration, a sensor may only needs to transmit data to its neighboring sensor/relay unit which may then transmit the received data, together with its own data or an output data processed from its own data and the data from the neighboring sensor to the next unit down the line and so on until reaching a telemetry, processing and/or power hub, which may be disposed on the seabed, a platform, at the surface and/or on a boat.

In the foregoing description, for the purposes of illustration, various methods and/or procedures were described in a particular order. It should be appreciated that in alternate embodiments, the methods and/or procedures may be performed in an order different than that described. It should also be appreciated that the methods described above may be performed by hardware components and/or may be embodied in sequences of machine-executable instructions, which may be used to cause a machine, such as a general-purpose or special-purpose processor or logic circuits programmed with the instructions, to perform the methods. These machine-executable instructions may be stored on one or more machine readable media, such as CD-ROMs or other type of optical disks, floppy diskettes, ROMs, RAMs, EPROMs, EEPROMs, magnetic or optical cards, flash memory, or other types of machine-readable media suitable for storing electronic instructions. Merely by way of example, some embodiments of the invention provide software programs, which may be executed on one or more computers, for performing the methods and/or procedures described above. In particular embodiments, for example, there may be a plurality of software components configured to execute on various hardware devices. Alternatively, the methods may be performed by a combination of hardware and software.

Hence, while detailed descriptions of one or more embodiments of the invention have been given above, various alternatives, modifications, and equivalents will be apparent to those skilled in the art without varying from the spirit of the invention. Moreover, except where clearly inappropriate or otherwise expressly noted, it should be assumed that the features, devices and/or components of different embodiments can be substituted and/or combined. Thus, the above description should not be taken as limiting the scope of the invention, which is defined by the appended claims.

What is claimed is:

1. A system for flow assurance and pipeline monitoring for a pipeline for flowing a flow mixture containing one or more hydrocarbons, comprising:
   a Doppler sensor configured for coupling with a section of the pipeline and to sense a Doppler profile of the section of the section of the pipeline, wherein the Doppler profile identifies moving regions and zero velocity regions across the section of the pipeline;
   a memory configured to store a baseline profile across the section of the pipeline;
   a processor configured to compare the Doppler profile with the baseline profile to determine properties of deposits or corrosion in the section of the pipeline; and
   a thermal probe coupled non-invasively with the section of the pipeline and in data communication with the processor, the thermal probe sensor configured to sense characteristics of the deposit from thermal conduction through a pipe wall of the section of the pipeline.

2. The system of claim 1, wherein the Doppler sensor is configured for non-invasive coupling with the section of the pipeline.

3. The system of claim 1, wherein the Doppler sensor is coupled to a bottom of the section of the pipeline.

4. The system of claim 1, wherein the Doppler sensor is configured to sense less than a couple of centimeters into the flow mixture flowing in the section of the pipeline.

5. The system of claim 4, further comprising:
   a depth management processor coupled with the Doppler sensor and configured to manage the sensing depth of the Doppler sensor, wherein the depth management processor processes the Doppler profile to determine the sensing depth.

6. The system of claim 1, wherein the baseline profile is a profile of the section of the pipeline prior to or when the section of the pipeline was installed.

7. The system of claim 1, wherein the baseline profile is a profile of the section of the pipeline with a known thickness of a pipe-wall of the pipe section or a known deposit thickness.

8. The system of claim 1, wherein the baseline profile is a previously produced Doppler profile.

9. The system of claim 1, wherein the Doppler sensor comprises transceiver means for generating a pulsed signal in the range 100 KHz to 10 MHz and matching means adapted to be coupled to the section of the pipeline to reduce or prevent reflections occurring from a pipe wall of the section of the pipeline in response to the pulsed signal.

10. The system of claim 9, wherein the transceiver means generates a narrow band ultrasonic signal.

11. The system of claim 9, wherein the Doppler sensor comprises signal processing means for analyzing reflected signals received by the transceiver means.

12. The system of claim 11, wherein the signal processing means comprises means for calculating energy contained in a Doppler frequency shifted part of a reflected signal.

13. The system of claim 11, wherein the signal processing means comprises range-gate channels.

14. The system of claim 9, wherein the transceiver means comprises a transceiver, the matching means is an impedance matching device, and the transceiver and impedance matching device are contained in a common housing.

15. The system of claim 14, wherein the common housing includes a frequency transparent material to allow signals from the transceiver to be emitted from the housing without distortion.

16. The system of claim 14, wherein the housing comprises a contact face for engaging with the section of the pipeline, the contact face having a groove of complimentary curvature to a pipe wall of the section of the pipeline so as to provide sufficient contact area between the housing and the section of the pipeline.

17. The system of claim 9, wherein the matching means has matching impedance that substantially matches an impedance of the pipe wall.

18. The system of claim 9, wherein the pulsed ultrasonic signal is emitted at an angle to the section of the pipeline, and wherein the angle is selected to provide for generation of a shear wave in the pipe wall.

19. The system of claim 1, further comprising:
an acoustic impedance sensor coupled with the section of the pipeline and configured to determine one of characteristics of the flow mixture, the characteristics of the deposit and characteristics of a corrosion of the section of the pipeline.

20. The system of claim 19, further comprising:
a control processor coupled with at least one of the Doppler sensor, the thermal probe sensor and the acoustic impedance sensor and configured to control operation of at least one of the Doppler sensor, the thermal probe sensor and the acoustic impedance sensor according to at least one of the characteristics of the flow mixture, the characteristics of the deposit and the characteristics of a corrosion of the section of the pipeline.

21. A method for flow assurance and pipeline monitoring for a pipeline for flowing a flow mixture containing one or more hydrocarbons, comprising:
sensing a Doppler profile through a section of the pipeline and any of the flow mixture in the section;
comparing the Doppler profile with a previous Doppler profile to determine any change in the properties of the section of the pipeline or the flow properties of the flow mixture through the section of the pipeline; and
using a thermal probe sensor coupled non-invasively with the section of the pipeline to sense characteristics of the deposit from thermal conduction through a pipe wall of the section of the pipeline.

22. The method of claim 21, wherein the step of sensing a Doppler profile comprises non-invasively coupling one or more Doppler sensors with the section of the pipeline and using the one or more Doppler sensors to measure the Doppler profile.

23. The method of claim 21, wherein the Doppler profile is sensed to less than one or two centimeter into the flow mixture.

24. The method of claim 23, further comprising:
managing the sensing depth of the Doppler sensor.

25. The method of claim 21, wherein the previous Doppler profile comprises a profile of the section of the pipeline prior to or when the section of the pipeline was installed.

26. The method of claim 21, wherein the previous Doppler profile comprises a profile of the section of the pipeline with a known thickness of a pipe-wall of the pipe section or a known deposit thickness.

27. The method of claim 21, further comprising:
using an acoustic impedance sensor non-invasively coupled with the section of the pipeline to acoustically determine one of characteristics of the flow mixture, the characteristics of the deposit and characteristics of a corrosion of the section of the pipeline.

28. The method of claim 27, further comprising:
controlling operation of at least one of the Doppler sensor, the thermal probe sensor and the acoustic impedance sensor according to at least one of the characteristics of the flow mixture, the characteristics of the deposit and the characteristics of a corrosion of the section of the pipeline.

* * * * *